US006756063B2

(12) United States Patent
Kiss

(10) Patent No.: US 6,756,063 B2
(45) Date of Patent: Jun. 29, 2004

(54) METHODS AND COMPOSITIONS FOR THE TREATMENT OF HUMAN AND ANIMAL CANCERS

(75) Inventor: Zoltan Kiss, Austin, MN (US)

(73) Assignee: Zoltan Laboratories, LLC, Austin, MN (US)

( * ) Notice: Subject to any disclaimer, the term of this patent is extended or adjusted under 35 U.S.C. 154(b) by 107 days.

(21) Appl. No.: 09/864,685

(22) Filed: May 24, 2001

(65) Prior Publication Data

US 2002/0177583 A1 Nov. 28, 2002

Related U.S. Application Data

(60) Provisional application No. 60/279,859, filed on Mar. 29, 2001.

(51) Int. Cl.[7] .......................... A61K 33/34; A61K 33/32
(52) U.S. Cl. ....................... 424/630; 424/638; 424/641; 424/643; 514/479; 514/491; 514/494; 514/499; 514/500
(58) Field of Search .................................. 424/630, 638, 424/641, 643, 642; 514/479, 491, 494, 499, 500, 428, 512, 513, 515, 568, 599

(56) References Cited

U.S. PATENT DOCUMENTS

| 4,564,675 A | | 1/1986 | Kurabayashi et al. |
| 4,645,661 A | | 2/1987 | Schonbaum |
| 4,745,109 A | | 5/1988 | Bednarski et al. |
| 5,023,253 A | | 6/1991 | Remers et al. |
| 5,686,436 A | | 11/1997 | Van Dyke |
| 5,698,583 A | * | 12/1997 | Cresecenti ................. 424/1.11 |
| 5,783,596 A | | 7/1998 | Medford et al. |
| 5,856,353 A | | 1/1999 | Tung et al. |
| 5,916,910 A | | 6/1999 | Lai |
| 5,919,816 A | * | 7/1999 | Hausheer et al. ........... 514/449 |
| 5,922,761 A | | 7/1999 | Lai |
| 5,958,918 A | | 9/1999 | Ewing et al. |
| 6,074,643 A | | 6/2000 | Barbera-Guillem |
| 6,231,852 B1 | * | 5/2001 | Bredesen ................... 424/94.4 |

FOREIGN PATENT DOCUMENTS

| WO | WO 00/35930 | 6/2000 | |
| WO | WO 00/61142 | * 10/2000 | .......... A61K/31/35 |

OTHER PUBLICATIONS

Product Information, Kamiya Biomedical Company, 1 pg., undated.
Burkitt, Mark J.; Bishop, Hugh S.; Milne, Lesley; Tsang, Shui Ying; Provan, Gordon J.; Nobel, C. Stefan I.; Orrenius, Sten; Slater, Andrew F. G., "Dithiocarbamate Toxicity toward Thymocytes Involves Their Copper–Catalyzed Conversion to Thiuram Disulfides, Which Oxidize Glutathione in a Redox Cycle without the Release of Reactive Oxygen Species," Archives of Biochemistry and Biophysics, 353, 73–84, 1998.
Orrenius, S.; Nobel, C. S. I.; van den Dobbelsteen, M. J.; Burkitt, M. J.; Slater, A. F. G., "Dithiocarbamates and the redox regulation of cell death." Biochemical Society Transactions, 24, 1032–1038, 1996.
Fürstenberger, G.; Amtmann, E.; Marks, F.; Sauer, G., "Tumor Prevention by a Xanthate Compound in Experimental Mouse–skin Tumorigenesis," Int. J. Cancer, 43, 508–512, 1989.
Kim, Chul Hoon; Kim, Joo Hee; Xu, Jan; Hsu, Chung Y.; Ahn, Young Soo, "Pyrrolidine Dithiocarbamate Induces Bovine Cerebral Endothelial Cell Death by Increasing the Intracellular Zinc Level," Journal of Neurochemistry, 72, 1586–1592, 1999.
Chinery, Rebecca; Brockman, Jeffrey A.; Peeler, Mark O.; Shyr, Yu; Beauchamp, R. Daniel; Coffey, Robert J., "Antioxidants enhance the cytotoxicity of chemotherapeutic agents in colorectal cancer: A p53–independent induction of $p21^{WAF1/CIP1}$ via C/EBPβ," Nature Medicine, 3, 1233–1241, 1997.
Nobel, C. Stefan I.; Kimland, Monica; Lind, Birger; Orrenius, Sten; Slater, Andrew F. G., "Dithiocarbamates Induce Apoptosis in Thymocytes by Raising the Intracellular Level of Redox–active Copper," The Journal of Biological Chemistry, 270, 26202–26208, 1995.
Erl, Wolfgang; Weber, Christian; Hansson, Göran K., "Pyrrolidine dithiocarbamate–induced apoptosis depends on cell type, density, and the presence of $Cu^{2+}$ and $Zn^{2+}$,"American Journal of Physiology, 278, C1116–C1125, 2000.
Chung, Kwang Chul; Park, Jae Hyun; Kim, Chul Hoon; Lee, Hyun Woo; Sato, Noboru; Uchiyama, Yasuo; Ahn, Young Soo, "Novel Biphasic Effect of Pyrrolidine Dithiocarbamate on Neuronal Cell Viability Is Mediated by the Differential Regulation of Intracellular Zinc and Copper Ion Levels, NF–kB, and MAP Kinases," Journal of Neuroscience Research, 59, 117–125, 2000.
Nobel, C. Stefan I., Burgess, David H.; Zhivotovsky, Boris; Burkitt, Mark J.; Orrenius, Sten; Slater, Andrew F. G., "Mechanism of Dithiocarbamate Inhibition of Apoptosis: Thiol Oxidation by Dithiocarbamate Disulfides Directly Inhibits Processing of the Caspase–3 Proenzyme," Chemical Research in Toxicology, 10, 636–643, 1997.

(List continued on next page.)

*Primary Examiner*—Frederick Krass
(74) *Attorney, Agent, or Firm*—Faegre & Benson LLP

(57) ABSTRACT

Methods and compositions for altering the viability of cells, particularly cancers in animals and humans are disclosed. The compositions of the present invention are formed from a set of components comprising one or more of the following: a dithiocarbonyl, preferably dithiocarbamate, compound; a divalent metal ion; a modulator of cellular glutathione levels; and an inhibitor of the phosphorylation of choline. The compositions described herein induce a relatively selective and rapid effect on the viability of cancer cells by inducing a mixture of apoptotic and necrotic cell death, with the dominant pathway being apoptosis. Particularly preferred active compositions comprise all four components, although combinations of fewer components can be fully effective in certain tumors.

29 Claims, 11 Drawing Sheets

OTHER PUBLICATIONS

McCabe, Jr., Michael J.; Jiang, Shun Ai; Orrenius, Sten, "Chelation of Intracellular Zinc Triggers Apoptosis in Mature Thymocytes," Laboratory Investigation, 69, 101–110, 1993.

Tsai, Jer–Chia; Jain, Mukesh; Hsieh, Chung–Ming; Lee, Wen–Sen; Yoshizumi, Masao; Patterson, Cam; Perrella, Mark A.; Cooke, Carol; Wang, Hong; Haber, Edgar; Schlegel, Robert; Lee, Mu–En, "Induction of Apoptosis by Pyrrolidinedithiocarbamate and N–Acetylcysteine in Vascular Smooth Muscle Cells," The Journal of Biological Chemistry, 271, 3667–3670, 1996.

Ragione, Fulvio Della; Cucciolla, Valeria; Borriello, Adriana; Pietra, Valentina Della; Manna, Caterina; Galletti, Patrizia; Zappia, Vincenzo, "Pyrrolidine Dithiocarbamate Induces Apoptosis by a Cytochrome c–Dependent Mechanism," Biochemical and Biophysical Research Communications, 268, 942–946, 2000.

Kiss, Zoltan; Crilly, Karan S.; Chung, Taeowan, "Stimulation of DNA Synthesis in Untransformed Cells by the Antiviral and Antitumoral Compound Tricyclodecan–9–yl–xanthogenate (D609)," Biochemical Pharmacology, 55, 915–918, 1998.

Amtmann, Eberhard; Müller, Karin; Knapp, Anita, Sauer, Gerhard, "Reversion of Bovine Papillomavirus–induced Transformation and Immortalization by a Xanthate Compound," Experimental Cell Research, 161, 541–550, 1985.

Sauer, Gerhard; Amtmann, Eberhard; Melber, Karl; Knapp, Anita; Müller, Karin; Hummell, Klaus; Scherm, Arthur, "DNA and RNA virus species are inhibited by xanthates, a class of antiviral compounds with unique properties," Proc. Natl. Acad. Sci. USA, 81, 3263–3267, 1984.

Chirney, Rebecca; Beauchamp, R. Daniel; Shyr, Yu; Kirkland, Susan C.; Coffey, Robert J.; Morrow, Jason D., "Antioxidants Reduce Cyclooxygenase–2 Expression, Prostaglandin Production, and Proliferation in Colorectal Cancer Cells[1]," Cancer Research, 58, 2323–2327, 1998.

Waxman, David J., "Glutathione S–Transferases: Role in Alkylating Agent Resistance and Possible Target for Modulation Chemotherapy–A Review[1],"Cancer Research, 50, 6449–6454, 1990.

Ploemen, Jan H. T. M..; van Ommen, Ben; van Bladeren, Peter J.; "Inhibition of Rat and Human Glutathione S–Transferase Isoenzymes by Ethacrynic Acid and its Glutathione Conjugate," Biochemical Pharmacology, 40, 1631–1635, 1990.

Ciaccio, Paul J.; Tew, Kenneth D.; LaCreta, Frank P., "Enzymatic conjugation of chlorambucil with glutathione by human glutathione S–transferases and inhibition by ethacrynic acid," Biochemical Pharmacology, 42, 1504–1507, 1991.

Tew, Kenneth D.; Bomber, Annette M.; Hoffman, Sandra J., "Ethacrynic Acid and Piriprost as Enhancers of Cytotoxicity in Drug Resistant and Sensitive Cell Lines[1]," Cancer Research, 48, 3622–3625, 1988.

O'Dwyer, Peter J.; LaCreta, Frank; Nash, Sherri; Tinsley, Peter W.; Schilder, Russell; Clapper, Margie L.; Tew, Kenneth D.; Panting, Lisa; Litwin, Samuel; Comis, Robert L.; Ozols, Robert F., "Phase I Study of Thiotepa in Combination with the Glutathione Transferase Inhibitor Ethacrynic Acid[1]," Cancer Research, 51, 6059–6065, 1991.

Lacreta, Frank P.; Brennan, James M.; Nash, Sherrie L.; Comis, Robert L.; Tew, Kenneth D., O'Dwyer, Peter J., "Pharmakokinetics and Bioavailability Study of Ethacrynic Acid as a Modulator of Drug Resistance in Patients with Cancer[1]," The Journal of Pharmacology and Experimental Therapeutics, 270, 1186–1191, 1994.

Kang, Y. James, "Buthionine Sulfoximine Enhances Glutathione–But Attenuates Glutamate–Stimulated Cell Proliferation," Cellular and Molecular Biology Research, 41, 131–136, 1995.

Liebmann, James E.; Hahn, Stephen M.; Cook, John A.; Lipschultz, Claudia; Mitchell, James B.; Kaufman, Dwight C., "Glutathione Depletion by $_L$–Buthionine Sulfoximine Antagonizes Taxol Cytotoxicity," Cancer Research, 53, 2066–2070, 1993.

Malewicz, Barbara; Mukherjee, Jagot J.; Crilly, Karan S.; Baumann, Wolfgang J.; Kiss, Zoltan, "Phosphorylation of ethanolamine, methylethanolamine, and dimethyl–ethanolamine by overexpressed ethanolamine kinase in NIH 3T3 cells decreases the co–mitogenic effects of etheanolamines and promotes cell survival," Eur. J. Biochem., 253, 10–19, 1998.

Schreck, Ralf; Meier, Beate; Männel, Daniela N.; Dröge, Wulf; Baeuerle, Patrick A., "Dithiocarbamates as Potent Inhibitors of Nuclear Factor kB Activation in Intact Cells," The Journal of Experimental Medicine, 178, 1181–1194, 1992.

Kastan, Michael B. "To oxidize or not to oxidize?" Nature Medicine, 3, 1192–1193, 1997.

Chinery, Rebecca; ; Beauchamp, R. Daniel; Shyr, Yu; Kirkland, Susan C.; Coffey, Robert J.; Morrow, Jason D., "Antioxidants Reduce Cyclooxygenase–2 Expression, Prostaglandin Production, and Proliferation in Colorectal Cancer Cells," Cancer Research, 58, 2323–2327, 1998.

Brennan, Paul; O'Neill, Luke A. J., "2–Mercaptoethanol restores the ability of nuclear factor $_k$B (NF$_K$B) to bind DNA in nuclear extracts from interleukin 1–treated cells incubated with pyrollidine dithicarbamate (PDTC)," Biochemical Journal, 320, 975–981, 1996.

Wu, Min; Lee, Hayyoung; Bellas, Robert E.; Schauer, Stephanie L.; Arsura, Marcello; Katz, David; FitzGerald, Mark J.; Rothstein, Thomas L.; Sherr, David H.; Sonenshein, Gail E., "Inhibition of NF–$_K$B/Rel induces apoptosis of murine B cells," The Embo Journal, 15, 4682–4690, 1996.

Trombetta, Louis D.; Toulon, Maureen; Jamall, I. Siraj, "Protective Effects of Glutathione on Diethyldithiocarbamate (DDC) Cytotoxicity: A Possible Mechanism," Toxicology and Applied Pharmacology, 93, 154–164, 1988.

Halstead, Jennifer; Kemp, Kathleen; Ignotz, Ronald A., "Evidence for Involvement of Phosphatidylcholine–Phospholipase C and Protein Kinase C in Transforming Growth Factor–β Signaling," The Journal of Biological Chemistry, 270, 13600–13603, 1995.

Schenk, H.; Klein, M.; Erdbrugger, W.; Droge, W.; Schulze–Osthoff, K., "Distinct Effects of Thioredoxin and Antioxidants on the Activation of Transcription Factors NF–kB and AP–1," Proc. Natl. Acad. Sci. USA, 91, 1672–1676, 1994.

Lees, G.J.; Cuajungco, M.P., Leong, W., "Effect of metal chalating agents on the direct and seizure–related neuronal death induced by zinc and kainic acid," Brain Research, 13, 108–117, 1998.

Koh, Jae–Young; Suh, Sang W.; Gwag, Byoung J.; He, Yong Y.; Hsu, Chung Y.; Choi, Dennis W., "The Role of Zinc in Selective Neuronal Death After Transient Global Cerebral Ischemia," Science, 272, 1013–1016, 1996.

Glassman, Armand B.; Rydzewski, Raymond S.; Bennett, Carol E. "Trace Metal Levels in Commercially Prepared Tissue Culture Media," Tissue and Cell, 12, 613–617, 1980.

Schütze, Stefan; Potthoff, Karin; Machleidt, Thomas; Berkovic, Dinko; Wiegmann, Katja; Krönke, Martin, "TNF Activates NF–kB by Phosphatidylcholine–Specific Phospholipase C–Induced "Acidic" Sphingomyelin Breakdown," Cell, 71, 765–776, 1992.

Müller–Decker, Karin; Doppler, Clemens; Amtmann, Eberhard; Sauer, Gerhard, "Interruption of Growth Signal Transduction by an Antiviral and Antitumoral Xanthate Compound," Experimental Cell Research, 177, 295–302, 1988.

Moellering, Douglas; McAndrew, Joanne; Hanjoong, Jo; Darley–Usmar, Victor M., "Effects of Pyrrolidine Dithiocarbamate on Endotherlial Cells: Protection Against Oxidative Stress," Free Radical Biology & Medicine, 26, 1138–1145, 1999.

Scozzafava, Andres; Mastrolorenzo, Antonio; Supuran, Claudiu T.; "Arylsulfonyl–N,N–diethyl–dithiocarbamates: A Novel Class of Antitumor Agents," Bioorganic & Medicinal Chemistry Letters, 10, 1887–1891, 2000.

* cited by examiner-

METHODS AND COMPOSITIONS FOR THE TREATMENT OF HUMAN AND ANIMAL CANCERS

CROSS REFERENCE TO RELATED APPLICATION

This application claims the benefit of U.S. Provisional Application 60/279,859, entitled METHODS AND COMPOSITIONS FOR THE TREATMENT OF HUMAN AND ANIMAL CANCERS, filed on Mar. 29, 2001.

FIELD OF THE INVENTION

This invention relates to methods and compositions for altering the viability of cells, particularly nonnormal or nonhealthy cells, such as those comprising various cancers in animals and humans. More particularly, the invention relates to the preparation and use of the compositions of the present invention to rapidly kill or weaken cancerous cells within or on the surface of an animal or human body. The invention also relates to methods to minimize metastatic growth potential of cancer cells derived from primary tumors during surgical intervention. Primarily intratumoral, but also systemic or parenteral treatments as well as pre-operative, post-operative, or topical treatment of cancers are contemplated. The present invention illustrates surprising and rapid effectiveness and relative specificity against a broad class of cancer cells and cancerous tissues over healthy cells.

BACKGROUND OF THE INVENTION

Despite vast advances in screening, lifestyle moderation, and therapeutic approaches, cancer continues to be one of the leading causes of death in the world. Drug toxicity, drug resistance, and the varying genetic backgrounds of different cancer sub-types have complicated the development of chemotherapeutics that are specifically cytotoxic to cancerous cells, yet minimally toxic to the patient.

Many currently available cancer treatments depend on the type, location, size and stage of the tumor, as well as numerous patient health-related issues. Typically, treatment may involve surgery, chemotherapy, and radiation, alone or in combination. Surgical removal of a cancerous tumor, for example breast tumors, is often desired in conjunction with chemotherapy and/or radiation, because the tumor may represent a burden to the patient's body.

During surgery, tumor cells often escape into the blood stream, leading to secondary tumors. Also the surgeon or radiologist may not succeed in removing/destroying the whole cancer tissue, leading to local recurrences. Therefore, even after seemingly successful treatment of a primary tumor, local recurrences and metastasis, i.e., the spread of malignant tumors to secondary sites, often represent further threats to the patient. It would be desirous to have methods and compositions that minimize the risk of metastasis and local recurrences, while at the same time present minimal toxic burden to the patient.

There remains a need for compositions with enhanced specificity and rapid cytotoxicity for a broad range of nonnormal or nonhealthy cells over healthy cells. In particular there remains a need for compositions and methods to treat and to prevent primary cancers and metastases that could be employed both locally, at the site of a primary tumor, and/or systemically, but that would present minimal toxic burden to the patient. Because of the heterogeneity of cancers, there further remains a need for a method to produce and to screen a library of active compositions from which a particular composition capable of altering the viability of a wide spectrum of cancerous cell types and sub-types may be chosen.

SUMMARY OF THE INVENTION

It is an object of the present invention to provide methods and compositions that alter the viability of a wide spectrum of nonnormal or nonhealthy cells, particularly cancers, but preferably that minimally affect the viability of healthy human cells. It has been found that the compositions and methods of the present invention demonstrate a surprisingly rapid, relatively specific, cytotoxicity for a broad range of nonnormal cells, particularly cancers, including but not limited to breast (both estrogen receptor positive and negative), epidermal, melanomal, colorectal, bladder, cervical, neuroblastomal, prostate, ovarian, endometrial, and placental cancers.

In practice, the compositions of the present invention are formed from a set of components comprising one or more of the following: (A) a dithiocarbonyl, preferably dithiocarbamate, compound; (B) a divalent metal ion; (C) a modulator of cellular glutathione levels; and (D) an inhibitor of the phosphorylation of choline, which can significantly change the composition of biological membranes. The biologically effective compositions described herein induce a selective and rapid effect on the viability of preferably, nonnormal cells, by inducing apoptotic or necrotic cell death, or both, with the dominant pathway being apoptosis. Particularly preferred active compositions comprise all four components, although combinations of fewer components can be fully effective in certain tumors. Such compositions have been found to be useful against a broad spectrum of cancerous cell lines while exhibiting less toxicity to healthy cells. Such compositions are thereby useful to treat tumors in vivo that are typically heterogeneous. The multi-component embodiments can be thus effective against the entirety of such tumors, whereas conventional chemotherapies often have more limited specificity. Compositions comprising less than all four components are also able to alter the viability of one or more particular cell lines.

In one aspect of the invention, compositions of the present invention are prepared by incorporating one or more of the components A, B, C, and D into the composition. The dithiocarbonyl component A, preferably a dithiocarbamate compound, of the composition usually has the formula: $(R_1)_m(R_2)$—Z—C(S)—S—Y wherein m is 0 or 1, but other structures can be envisioned. For example, a dithiocarbamate moiety can be inserted into fatty acid chains, or between the phosphate group and the polar headgroup, or at the end of the polar headgroup in a phospholipid molecule.

Y is chosen from the group consisting of hydrogen, a pharmaceutically acceptable cation, a physiologically cleavable leaving group, a targeting moiety, or a pharmaceutically active drug, including a chemotherapeutic drug. In a preferred embodiment, Y represents a pharmaceutically acceptable cation, and may represent all or a portion of the component B listed above.

Z may be preferably chosen from either O or N, but if Z is O, then m=0. R1 and R2 may be independently chosen from the group consisting of hydrogen; or C1–C24 straight, branched, or cyclic alkyl, alkenyl, aryl, acyl, alkaryl, aralkyl, or alkoxy groups, optionally substituted with ester, ether, halogen, sulfate, hydroxy, or phosphate groups. R1 and R2 may be optionally connected via a bridge such as —$(CH)_n$—, wherein n is 3–8, so that the resulting structure is heterocyclic, and may be optionally substituted on any of the carbon atoms of the ring. Representative substitutents include, for example, C1–C10 straight, branched, or cyclic alkyl, aryl, aryalkyl, or alkaryl groups, optionally substituted with hydroxy, halo, phosphate, sulfate, or sulfonate groups.

Preferred dithiocarbonyl compounds of the present invention include diethyldithiocarbamate (DEDC); tricyclo-[5.2.1.O$^{2,6}$]-decyl(9[8]-xanthogenate (also known commonly as D609); tetraethylthiuram disulfide (also known commonly as Disulfuram, $((C_2H_5)_2NCS_2-]_2))$; and pyrrolidinedithiocarbamate (PDC). Other representative dithiocarbonyl compounds are set forth in U.S. Pat. No. 5,783,596, incorporated herein by reference.

The present compositions also may incorporate a metal ion component B. In particular, the dithiocarbonyl components of the present invention may be complexed with the metal cation component B. Suitable metal cations include $Cu^{2+}$ and $Zn^{2+}$. Most preferably, $Zn^{2+}$ is employed.

The compositions of the present invention may also incorporate a component C to affect the intracellular redox state of nonnormal or nonhealthy cells. In particular, it has been surprisingly discovered that chemical and enzymatic modulators of cellular glutathione (GSH) levels enhance the efficacy of the compositions of the present invention. Those compounds that deplete cellular glutathione are preferred as component C, including ethacrynic acid (EA), L-buthionine-S,R-sulfoximine (BSO), diethylmaleate, 2-cyclohexene-1-one, and 1-chloro-2,4-dinitrobenzene (CDNB). Most preferably, EA is employed as component C, because in toxicological studies it appears to be relatively well tolerated by humans.

While not wishing to be bound by any theory, the component C of the present invention seems to affect the cellular concentration of reduced glutathione (GSH). GSH is perhaps the most important protective antioxidant against oxidants and electrophilic compounds. The GSH redox system is crucial in maintaining intracellular GSH/GSSG homeostasis. This system uses GSH as a substrate in detoxification of peroxides such as hydrogen peroxide and lipid peroxides, reactions which involve glutathione peroxidase. The reactions generate oxidized GSH (i.e., GSSG), which is reduced to GSH by glutathione reductase in a reaction requiring the hexose monophosphate-shunt pathway utilizing reduced nicotinamide adenine dinucleotide phosphate (NADPH). Glutathione also reduces nonenzymatically a number of substances, such as peroxides or free radicals.

Through a widely distributed enzyme, glutathione S-transferase (GST), GSH participates in the detoxification of many substances, i.e., organic halides, fatty acid peroxides, etc. In a GST-catalyzed reaction, GSH reacts with such compounds, followed by cleavage of GSH's glutamyl and glycyl residues and then acetylation by acetyl-CoA to give a mercapturic acid. Ethacrynic acid (EA) and 1-Cl-2, 4-dinitrobenzene are substrates for the GST-catalyzed conjugation reaction, resulting in the depletion of cellular GSH. Because the present compositions are likely to act via oxidative shock, depletion of cellular glutathione by these compositions inhibits the cellular defense system, and probably enhances the efficacy of the compositions.

It has been further found that inhibitors of the phosphorylation of choline, which is involved in the formation of the major membrane phospholipid phosphatidylcholine, in some cases surprisingly enhance the efficacy of the compositions of the present invention. Preferably, such an inhibitor comprises component D, and is incorporated into the compositions of the present invention. A preferred embodiment of component D is dimethylethanolamine (DMETN). A further advantage of using DMETN is that it also inhibits proliferation of several cancer cell lines (T-47D, 2R-75-1, A431, MDA-MB-231, $AN_3Ca$, $CaOV_3$) while generally increasing proliferation of normal cells. Therefore, should some cancer cells survive surgery, the presence of DMETN would be expected to inhibit their growth.

It is another object of the present invention to provide methods for preoperative and post-operative treatment of cancerous cells and metastases. Because the compositions of the present invention alter the viability of nonnormal cells with some selectivity, the compositions may be used to treat primary tumors as well as metastases. The compositions are designed mainly for intratumoral application, but they may be also used either systemically or parenterally (e.g., i.v., i.p., subcutaneously, topically, transdermally, etc.). The compositions also may be used to prevent metastatic spread of cancerous cells from a primary tumor by rapidly inducing apoptotic and/or necrotic cell death in the tumor prior to surgical intervention.

It is another object of the invention to provide methods for altering the viability of one or more nonnormal or nonhealthy cells by providing a composition according to the present invention and exposing the cells, preferably cancerous cells, to the composition. Exposure may be through systemic administration of the compositions, or parenterally through topical, transdermal, or, preferably, intratumoral administration.

It is a further object of the present invention to provide methods for generating libraries of active compositions from which a preferred active composition comprising one or more components A, B, C, and D may be chosen. The method is employed to generate a preferred composition that is specifically tailored to be maximally effective in altering the viability of a particular cancer, while preferably exhibiting minimal alteration to the viability of normal cells. Alternatively, the particular composition may be chosen to be more broadly effective against a range of cancers, while nonetheless preferably remaining minimally toxic to healthy cells. The method is comprised of steps wherein a set of components that includes at least two, preferably three, and most preferably all four of the components A, B, C, and D is provided for incorporation into a plurality of test compositions. The test compositions so generated may vary based on the components incorporated, their concentrations, and the like. The test compositions so generated are then examined to determine if any induces a desired biological effect against one or more nonhealthy or nonnormal cell types. Based on the results, the desired composition is selected from among said test compositions. The desired composition may be used, for example, to treat a heterogeneous cancerous tumor, or alternatively to treat a more homogeneous cancerous tumor.

Finally, it is yet another object of the present invention to provide methods to treat primary tumors as well as metastases by combining the compositions with other, already tested, chemotherapeutic agents including but not limited to: cyclophosphamide, doxorubicin, vinorelbine, cisplatin, paclitexel, topotecan, 5'-fluorouracyl, epirubicin, trimetrexate, etc. Such combination treatments may allow the use of these anticancer agents at lower concentrations, thereby decreasing their toxic side effects.

In addition, the present compositions may be used in combination with radiotherapy; again, such combinations may allow the use of lower dosage levels of the composition chemicals and lower levels of radiation, which would decrease any toxic side effects.

DETAILED DESCRIPTION OF THE INVENTION

I. Definitions

Figure 1A:
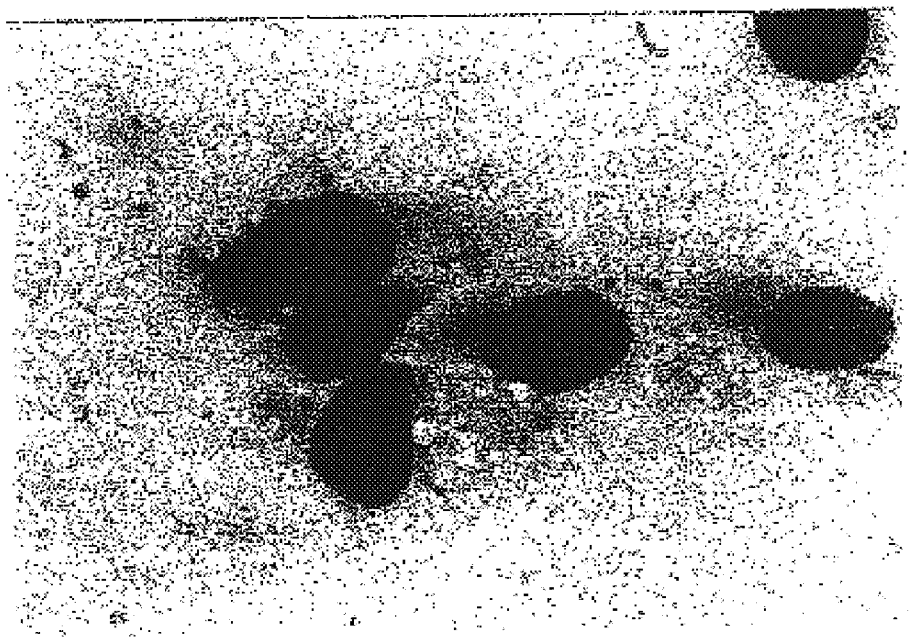
FIGS. 1a and 1b. Comparison of MXT mouse mammary carcinoma tumor cells derived from untreated tumors (developed in mice) (FIG. 1a), and tumor cells derived from tumors treated with a composition comprising pyrrolidinedithiocarbamate (PDC, 50 $\mu$M), zinc (150 $\mu$M), ethacrynic acid (100 $\mu$M) and dimethylethanolamine (6 mM) for 4 h (FIG. 1b). At least 90% of the cells were dead after treatment, as indicated by cellular morphology, lysis, membrane blebbing, chromatin condensation, and the appearance of apoptotic bodies. Approximately 80% of the cells which died did so via an apoptotic mechanism. When cells derived from treated tumors were incubated for 3 days or 3 weeks, no viable tumor cells were found; under comparable conditions control tumor cells grew as expected.
Figure 1B:
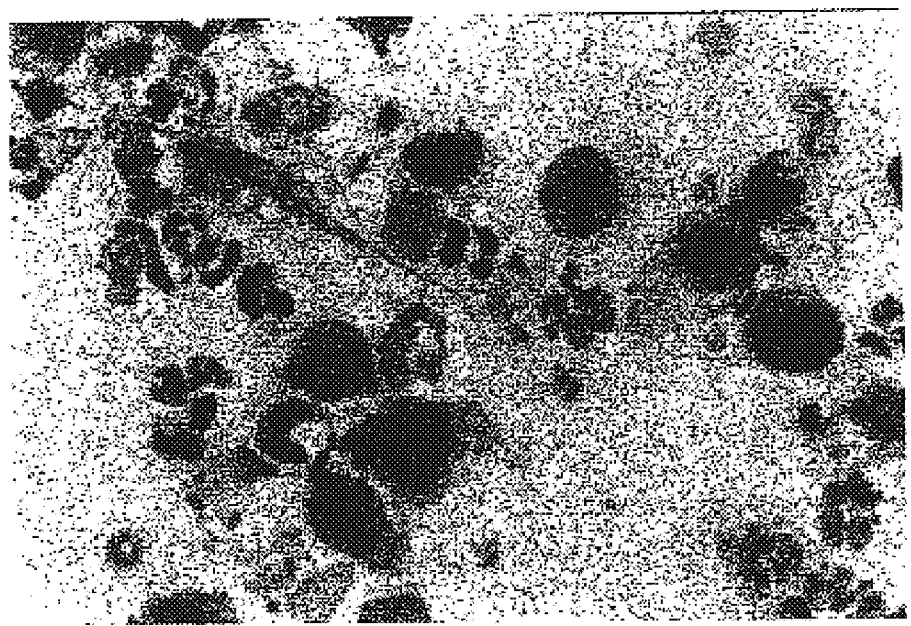
Figure 2A:
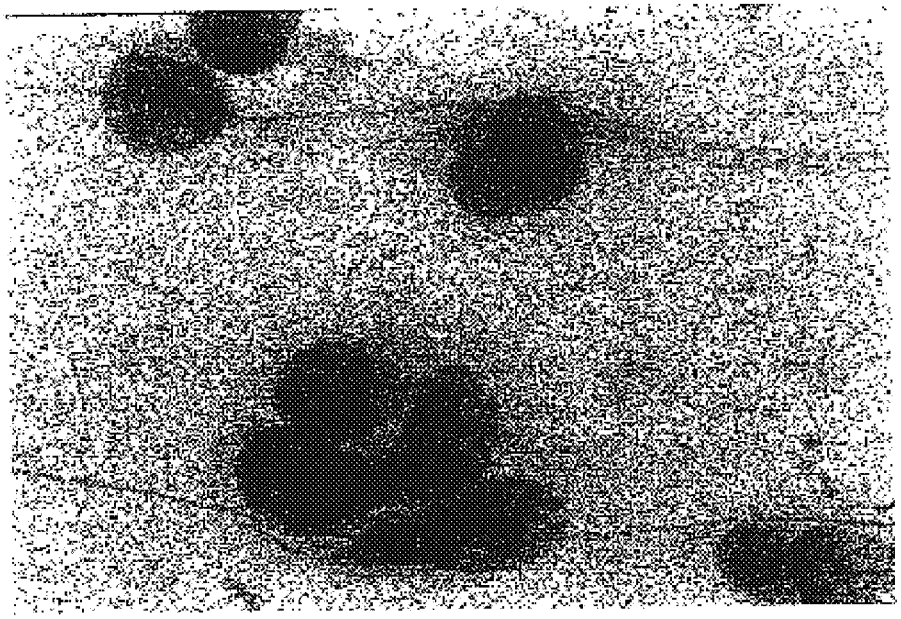
FIGS. 2a and 2b. Comparison of C26 mouse colon tumor cells derived from untreated tumors (developed in mice) (FIG. 2a), and tumor cells derived from tumors treated with a composition comprising PDC (50 $\mu$M), zinc (150 $\mu$M), ethacrynic acid (100 $\mu$M) and dimethylethanolamine (6 mM) for 4 h (FIG. 2b). About 100% of the cells were dead after treatment, as indicated by cellular morphology, lysis, membrane blebbing, chromatin condensation, and the appearance of apoptotic bodies. Approximately 80% of the cells appeared to die via an apoptotic mechanism. When cells derived from treated tumors were incubated for 3 days or 3 weeks, no viable tumor cells were found.
Figure 2B:
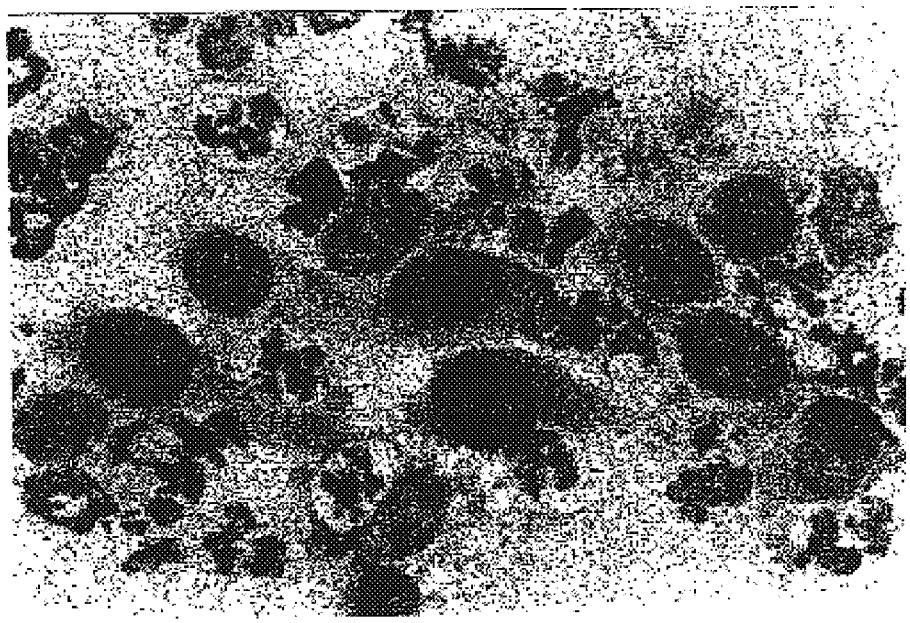

Necrosis, as used herein, may be indicated by cellular morphological changes, including one or more of the following: removal of the cell from the subsurface stratum, cell rounding, cell swelling, and cell lysis; necrosis may also be indicated by cessation of DNA synthesis and cellular proliferation. Necrosis is not accompanied by nuclear changes.

Apoptosis, as used herein, is a mechanism of cell death known as programmed cell death, and is characterized by one or more of the following: chromatin condensation, cleavage of DNA into fragments, cell shrinkage, and membrane blebbing. In the mechanism, the apoptotic cell eventually falls apart with the formation of well-enclosed, apoptotic bodies.

II. Active Compositions

The compositions and methods of the present invention demonstrate surprisingly rapid cytotoxicity, with some specificity, for a broad range of nonnormal cells, particularly cancers, including but not limited to breast (both estrogen receptor positive and negative), epidermal, melanomal, colorectal, bladder, cervical, neuroblastomal, prostate, ovarian, endometrial, and placental cancers. The use herein of compositions comprising dithiocarbonyl, particularly dithiocarbamate (DTC), components, including their metal complexes, alone or in combination with cellular redox and growth cycle modulators, results in biologically effective compositions. These compositions induce a selective and rapid effect on the viability of nonnormal cells, preferably by inducing apoptotic or necrotic cell death, or both, with apoptosis representing the predominant mechanism of cell death. The compositions are used preferably intratumorally, but may be used also either systemically or parenterally, and either alone or in combination with surgical procedures, radiation, or various chemotherapeutic compositions.

In practice, the compositions of the present invention are comprised of one or more of the following components: (A) a dithiocarbonyl compound, preferably a dithiocarbamate; (B) a divalent metal ion; (C) a modulator of cellular glutathione; and (D) an inhibitor of the phosphorylation of choline.

Component A, the dithiocarbonyl compounds, particularly dithiocarbamates, of the present invention generally have the formula: $(R_1)_m(R_2)$—Z—C(S)—S—Y, wherein m is 0 or 1.

$R_1$, $R_2$, Z and Y are selected by one of skill in the art to maximize the efficacy of the compound and may be varied to modulate the size, charge, hydrophilicity, toxicity, bioavailability, plasma distribution, excretion pathway, stability, tissue distribution, pharmacokinetics, and pharmacodynamics of the molecule. Preferably the compounds have higher affinity and specificity for, and ability to alter the viability of, nonnormal cells, particularly cancer cells, rather than normal, healthy cells.

Y is selected from the group consisting of hydrogen, an enzymatically or physiologically cleavable leaving group, a targeting moiety, or a pharmacologically active drug, including a chemotherapeutic drug. Suitable linking moieties may optionally be employed to attach the cleavable leaving groups, targeting moieties, or pharmaceutically active drug to the dithiocarbonyl compound. Linking moieties are divalent groups that link the residues and include, but are not limited to, C1–C15 straight, branched, or cyclic alkyl, alkenyl, aryl, or polyalkyleneoxy groups, optionally substituted with halo, hydroxy, phosphate, sulfate, or sulfonate groups. Preferably the linking group does not affect either the affinity, specificity, or efficacy of the composition.

In a preferred embodiment, Y represents a pharmacologically acceptable cation. Pharmacologically acceptable cations include, but are not limited to, sodium, potassium, magnesium, calcium, aluminum, zinc, bismuth, barium, copper, cobalt, nickel, cadmium; ammonia, nitrogenous base derivatives, and heterocyclic bases.

If Y represents a physiologically cleavable leaving group, then the intact dithiocarbamate compound (including Y) represents a prodrug form. Physiologically cleavable leaving groups refer to moieties that may be cleaved in vivo from the molecule. Preferably the leaving groups will be cleaved under in vivo conditions and will degrade within a reasonable time period (within 2 h.) after application or contact with the cells or tissue of interest. Physiologically cleavable leaving groups include, but are not limited to, alkyl, acyl, ester, carboxy, phosphate, diphosphate, phosphonate, sulfate, or sulfonate moieties; or a physiologically cleavable polymer, including synthetic and natural proteins or polypeptides; random or block polymers and copolymers, including, for example, copolymers of amino acids such as poly-lysine; polyethyleneglycol and derivatives; polysaccharides; polyglycolic acid; polyorthoesters; or albumin or collagen, including fragments or modified versions; fatty acids, phospholipids, or other lipids.

Representative targeting moieties include, but are not limited to, antibodies and antibody fragments, including humanized versions; peptides or proteins, including glycosylated versions; oligonucleotides (RNA, DNA, or PNA based); polysaccharides; folate; or organic functionalities with affinities for serum proteins or proteins expressed by cancerous cells. In a preferred embodiment, the targeting moiety targets the dithiocarbamate to a desired cancerous cell line.

Z may be preferably chosen from either 0 or N, but if Z is 0, then m=0. $R_1$ and $R_2$ may be independently chosen from the group consisting of hydrogen; or C1–C24 straight, branched, or cyclic alkyl, alkenyl, aryl, acyl, alkaryl, aralkyl, or alkoxy groups, optionally substituted with ester, ether, halogen, sulfate, hydroxy, or phosphate groups. $R_1$ and $R_2$ may be optionally connected via a bridge such as —(CH$_2$)$_n$—, wherein n is 3–8, so that the resulting structure is heterocyclic, and may be optionally substituted on any of the carbon atoms of the ring with C1–C10 straight, branched, or cyclic alkyl, aryl, aryalkyl, or alkaryl groups, optionally substituted with hydroxy, halo, phosphate, sulfate, or sulfonate groups.

Preferred dithiocarbonyl compounds of the present invention include diethyldithiocarbamate (DEDC); tricyclo-[5.2.1.O$^{2,6}$]-decyl(9[8]-xanthogenate (D609); disulfuram; and pyrrolidinedithiocarbamate (PDC). In general, the active dithiocarbonyl, particularly dithiocarbamate, components used in the present compositions are either commercially available or can be prepared using known synthetic methods. Other examples of dithiocarbonyl compounds are set forth in U.S. Pat No. 5,783,596, incorporated herein by reference.

A particularly preferred class of dithiocarbonyl components for incorporation into the compositions of the present invention is the dithiocarbamate class. Dithiocarbamates (DTCs) are low molecular weight thiol molecules that can chelate metals (particularly $Zn^{2+}$ and $Cu^{2+}$) and react with available sulfhydryl groups. They have been used traditionally as insecticides, fungicides, antivirals, metal-chelators, and antioxidants. Their antioxidant potential is a result of both their metal chelating ability and their ability to counteract the toxic effects of free radical damage, as both radical scavengers and as modulators of the redox state of intracellular thiols. See S. Orrenius, C. S. I. Nobel, D. J. van den Dobbelsteen, M. J. Burkitt, and A. F. G. Slater, "Dithiocarbamates and the redox regulation of cell death", Biochem. Soc. Trans. 24, 1032–38 (1996).

As antioxidants, some DTCs are thought to have chemopreventive properties (see G. Furstenberger, E. Amtmann, F. Marks, and G. Sauer, "Tumor Prevention by a Xanthate Compound in Experimental Mouse-Skin Tumorigenesis", Int. J. Cancer 43:508–12 (1989)) and have been used as potentiators of traditional chemotherapeutics (see R. Chinery, J. A. Brockman, M. O. Peeler, Y. Shyr, R. D. Beauchamp, and R. J. Coffey, "Antioxidants enhance the cytotoxicity of chemotherapeutic agents in colorectal cancer: a p53-independent induction of p21 via C/EBPB", Nature Medicine 3(11):1233–41 (1997)). More recently, DTCs have been shown to have pro-oxidant activities in cells, most likely through the recruitment of redox active metal ions into the cell. See C. H. Kim, J. H. Kim, J. Xu, C. Y. Hsu, and Y. S. Ahn, "Pyrrolidine Dithiocarbamate Induces Bovine Cerebral Endothelial Cell Death by Increasing the Intracellular Zinc Level", J. Neurochem. 72(4):1586–92 (1999); C. S. I. Nobel, M. Kimland, B. Lind, S. Orrenius, and A. F. G. Slater, "Dithiocarbamates Induce Apoptosis in Thymocytes by Raising the Intracellular Level of Redox-active Copper", J. Biol. Chem. 270(44): 26202–08 (1995).

Prior studies of the effect of DTCs on cell survival were conflicting, and demonstrated that cell type, availability of metal cations or competitive chelators, cell density, and cellular redox state were significant variables in the results.

(See W. Erl, C. Weber, and G. K. Hansson, "Pyrrolidine dithiocarbamate-induced apoptosis depends on cell type, density and the presence of $Cu^{2+}$ and $Zn^{2+}$", Am. J. Physiol. Cell. Physiol. 278(6): C1116–24 (2000).) DTCs have been shown to both inhibit and induce Nuclear Factor kappa-B (NF-κB) and other cell cycle proteins in the cell, leading to the proposal that DTCs can mediate cell death through an apoptotic (programmed cell death) mechanism. DTCs have been shown to induce apoptosis in cerebral endothelial cells, hepatocytes, smooth muscle cells, and thymocytes. See, C. H. Kim, J. H. Kim, J. Xu, C. Y. Hsu, and Y. S. Ahn, "Pyrrolidine Dithiocarbamate Induces Bovine Cerebral Endothelial Cell Death by Increasing the Intracellular Zinc Level", J. Neurochem. 72(4):1586–92 (1999); C. S. I. Nobel, M. Kimland, B. Lind, S. Orrenius, and A. F. G. Slater, "Dithiocarbamates Induce Apoptosis in Thymocytes by Raising the Intracellular Level of Redox-active Copper", J. Biol. Chem. 270(44): 26202–08 (1995). Other studies demonstrate an inhibitory effect on apoptosis, or a biphasic effect with an inhibition followed by an induction of apoptosis (see K. C. Chung, J. H. Park, C. H. Kim, H. W. Lee, N. Sato, Y. Uchiyama, and Y. S. Ahn, "Novel Biphasic Effect of Pyrrolidine Dithiocarbamate on Neuronal Cell Viability is Mediated by the Differential Regulation of Intracellular Zinc and Copper Ion Levels, NF-κB, and MAP Kinases", J. Neuro. Res. 59:117–25 (2000).) Overall, the prior art indicated that the interplay between cellular oxidative stress, the pro- or anti-oxidant capability of the DTC, and the redox state of the cell is not well understood. See, C. S. I. Nobel, D. H. Burgess, B. Zhivotovsky, M. J. Burkitt, S. Orrenius, and A. F. G. Slater, "Mechanism of Dithiocarbamate Inhibition of Apoptosis: Thiol Oxidation by Dithiocarbamate Disulfides Directly Inhibits Processing of the Caspase-3 Proenzyme", Chem. Res. Toxicol. 10:636–43 (1997).

While not wishing to be bound by any theory, it is believed that the compositions of the present invention optimally balance this sensitive and fluctuating interplay between the anti- and pro-oxidant capacities of the dithiocarbonyl components and the redox states of the cancer cells. The incorporation of the dithiocarbonyl components into the compositions of the present invention results in a more predictable and maximally effective induction of apoptotic or necrotic cell death, or a mixture of both.

Other preferred dithiocarbonyl components for use in the compositions of the present invention are dimers of the dithiocarbonyl compounds described previously. Such dimers may be represented by the formula: $(R_1)_m(R_2)Z$—C(S)—S—S—C(S)—$Z(R_1)_m(R_2)$. A preferred embodiment is Disulfuram, which is a dimer of DEDC currently used for the treatment of alcohol abuse.

The present compositions also may incorporate a metal ion component B. In particular, the dithiocarbonyl components of the present invention may be complexed with the metal cation component B prior to use. Suitable metal cations include $Cu^{2+}$ and $Zn^{2+}$. Most preferably, $Zn^{2+}$ is employed. It is believed that complexation of the metal ion by the dithiocarbonyl component facilitates uptake of the cation into, for example, cancerous cells; upon dissociation of the metal cation, destructive oxidative events are catalyzed by the cation. Alternatively, the dithiocarbonyl ligand may be uncomplexed with metal prior to use, and may bind available intracellular or serum metal cations in vivo.

The compositions of the present invention may also incorporate a component C that affects the intracellular redox state of nonnormal or nonhealthy cells. It has been surprisingly discovered that chemical and enzymatic modulators which are known to decrease the cellular glutathione levels enhance the efficacy of the compositions of the present invention. In some circumstances, the use of such compounds alone results in a significant reduction in cellular viability. While not wishing to be bound by any theory, it is believed that component C inhibits the strong anti-oxidant defense mechanism of cells in response to the oxidative stress induced by the dithiocarbonyl components when complexed to zinc or copper cations. Particularly, those compounds that deplete cellular glutathione are preferred, including ethacrynic acid (EA), L-buthionine-S,R-sulfoximine (BSO), diethylmaleate, 2-cyclohexene-1-one, and 1-chloro-2,4-dinitrobenzene (CDNB). Most preferably, EA is employed, because in human trials it appears to be tolerated. These compounds are commercially available from, e.g., Sigma, or are prepared using known synthetic methods.

It has been further found that inhibitors of the phosphorylation of choline, which is involved in the formation of the major membrane phospholipid phosphatidylcholine, surprisingly enhance the efficacy of the compositions of the present invention in several cancer cell lines. Preferably, such an inhibitor comprises component D and is incorporated into the compositions of the present invention. A preferred embodiment of component D is dimethylethanolamine (DMETN), which has the additional property to selectively inhibit proliferation of certain cancer cells.

Particularly preferred compositions for intratumoral applications comprise all four components A, B, C, and D. It has been found that compositions comprising all four components are capable of altering the viability of a broad range of nonnormal cells, including a broad spectrum of cancerous types and sub-types. Preferably, the compositions are comprised of concentrations between about 5–200 μM of the dithiocarbonyl compound component A, about 20–500 μM of the metal cation component B, about 10–300 μM of the modulator of the level of cellular glutathione component C, and about 3–40 mM of component D, DMETN. A particularly preferred embodiment comprises about 10–100 μM of PDC, about 20–200 μM zinc, about 10–100 μM of EA, and about 3–10 mM DMETN.

It has further been found that some compositions comprising fewer than all 4 components A, B, C, and D exhibit surprising efficacy against certain cancers. For example, (a) For rapid (within about 2 h.) and effective (about 100%) killing of human breast cancer cells (MDA-MB-231 cell line), a preferred composition comprises about 10–100 μM EA, about 5–50 μM PDC, and about 50–200 μM zinc.

For slow (within about 75 h. treatment) but effective (about 100%) killing of human breast cancer cells (MDA-MB-231 line), a preferred composition comprises about 10 μM EA and about 20 μM PDC.

(b) For rapid (within about 2 h.) and effective (about 100%) killing of human breast carcinoma cells (T-47D cell line), another preferred composition comprises about 50–200 μM EA.

For slow (within about 75 h. treatment) but effective (about 100%) killing of human breast cancer cells (T-47D cell line), a preferred composition comprises about 10–50 μM EA and about 10–50 μM PDC.

(d) For rapid (within about 160 min.) and effective (about 90–100%) killing of multi drug-resistant human breast cancer cells (MCF-7/MDR1 cell line), a preferred composition comprises about 30–80 μM EA, about 10–50 μM PDC, and about 30–80 μM zinc.

Mammals, particularly humans, may be treated by administering to the patient an effective amount of one of the compositions described herein or a pharmaceutically acceptable derivative or salt thereof in a pharmaceutically acceptable carrier or diluent. The active compositions may be administered by any appropriate route, including systemically, orally, parenterally, intravenously, subcutaneously, topically, intradermally, or by direct intratumoral injection. At higher concentrations of these drug combinations, aimed at rapid killing of cancer cells, intratumoral application is the most preferred route of delivery. At lower, less toxic, concentrations, other delivery methods may be employed.

Pharmaceutically acceptable salts include salts that retain the desired activity and exhibit minimal undesired toxicities. Representative examples include salts formed from organic acids or organic cations.

The active composition is included in a pharmaceutically acceptable carrier or diluent, in an amount sufficient to deliver to the patient a therapeutically effective amount without causing serious toxic side effects. If administered intravenously, preferred carriers are physiological saline or phosphate buffered saline (PBS) or various liposomal compositions. The preferred dose will depend on the route of administration and the method of treatment. If the composition is used either pre- or post-operatively, e.g. by direct injection into the tumor or its blood supply, or by topical application to the surgical site, then the four components will be generally used in the following concentration ranges expressed as $\mu g/cm^3$ tumor volume: DTC, about 0.3–10 $\mu g/cm^3$; EA, about 1–+$\mu g/cm^3$; zinc, about 0.5–20 $\mu g/cm^3$; and DMETN, about 10–250 $\mu g/cm^3$.

If employed systemically, the active composition should be administered to achieve and to maintain peak plasma concentrations of about 5–50 $\mu M$ of component A, depending on the tumor and the length of administration. For longer systemic administration (e.g., for 36–72 h. periods), preferably a peak plasma concentration of about 2–20 $\mu M$ is maintained. The active compositions most likely will be infused over a longer time period (i.e. 36–72 hours), although they might be injected as a bolus in certain situations.

As recognized by those of skilled in the art, dosage values will vary with the absorption, excretion, inactivation, toxicity, and distribution profiles of the drug, as well as with the severity of the illness to be treated, and may be varied according to individual need and the judgment of the health care professional. The concentration ranges set forth herein are only exemplary and not intended to limit the scope or practice of the invention. Thus, for example, lower dosages of the compositions described herein might be coupled with longer exposures in order to maximize the amount of cell death induced in cancerous cells while ensuring the health of normal cells. Alternatively, lower dosages might be used in combination with other chemotherapeutic agents.

Topical administration includes, but is not limited to, lotions, ointments, creams, gels, transdermal patches, suspensions, sprays, powders, pastes, slow-release or controlled-release formulations, including liposomal or microsphere formulations, aerosols, suppositories, and the like. The composition must be sufficiently absorbed by the skin or tissue of interest to render a therapeutic effect at the site. Thickening agents may be used to prepare topical compositions and include petrolatum, beeswax, xanthan gum, polyethylene glycol, lanolin, squalene, many of which are commercially available. In general, many methods for the preparation of topical formulations are well known to those skilled in the art.

Solutions or suspensions used for parenteral, intradermal, subcutaneous, or topical application can optionally include a sterile diluent, such as water, saline, fixed oils, polyethylene glycols, glycerine, antibacterial agents such as benzyl alcohol or methyl parabens, or buffers.

III. Methods of Use

The compositions of the present invention can be used to decrease the viability of nonnormal or nonhealthy cells, particularly those which constitute primary and secondary tumors. The compositions may be used both focally, at the site of a primary tumor, or systemically. The use of the compositions described herein preferably results in a rapid and relatively specific alteration of cellular viability, specifically the induction of apoptotic and necrotic cell death, in cancerous cells preferably over noncancerous cells. As used herein, necrosis is represented by morphological changes, including, particularly, the removal of the cell from the subsurface stratum, cessation of DNA synthesis, cell proliferation, cell rounding, and cell lysis. Apoptosis, also known as programmed cell death, as used herein, is characterized by chromatin condensation, cleavage of DNA into fragments, cell shrinkage, membrane blebbing, and formation of apoptotic bodies.

Most preferably, the compositions of the present invention are used intratumorally in conjunction with the surgical removal of tumors and post operational radiotherapy. In order to minimize the potential for metastases to develop and to weaken or kill existing primary tumors and metastases, the compositions are preferably used pre-operatively; however, they may also be used during the operation, and/or postoperatively, optionally in conjunction with traditional radiation or chemotherapeutic techniques. A composition comprised of one or more of the components described previously is allowed to contact the cancer cells in the tumor of interest. Depending on the nature, and more particularly, the size, of the cancerous tumor, this contact may occur through pre-operative topical treatment via lotions, creams, and the like, or transdermal patches (i.e., for skin cancers), all of which comprise the active composition. Alternatively, the surgeon may inject the compositions once or repeatedly into multiple sites in the tumorous tissue or introduce the composition systemically into the tumor's blood supply (i.e., for breast cancers) in order to expose the tumor to an effective dose of the composition.

For pre-operative treatment, the components will generally be dissolved in physiological saline or will be enclosed in liposomes or other delivery systems or formulations. The compositions are applied in a volume which constitutes up to 10% of the total volume of the tumor, depending on the size and quality of the tumor. Preferably, the length of time between injection and surgical removal of the tumor is about 1 to 4 hours. The treatment, whether systemic, parenteral, or intratumoral, exposes preferably 50%, even more preferably 90%, and most preferably 100%, of the tumor cells with an effective dose of the active composition. As will be understood by one of those skilled in the art, both the dosage and the number of treatments will be dependent on the type of tumor and the method of administration of the composition (e.g., whether intratumorally or systemically). Intratumoral application may be performed once, or maybe repeated several times over a period of time, depending on the test results (rapid microscopic analysis of cells).

The compositions of the present invention may also be used postoperatively, either by themselves or in conjunction with radiation or chemotherapies, in order to induce cell death (e.g., apoptosis or necrosis, or both) in any cells of the primary tumor or any metastatic seed cells remaining after surgery. A composition comprising one or more of the components described previously is allowed to contact the surgical site after the removal of the primary tumor. The composition may contact this surgical site either by systemic or parenteral means. Preferably, whether the treatment is parenteral or systemic, greater than 50% of the surface area of the surgical site or of the blood flow to the surrounding tissue is exposed to the active composition; more preferably, greater than 90% is exposed.

Of course, one of skilled in the art will recognize that the optimal treatment might involve the use of both pre-operative and post-operative methods in order to ensure optimal induction of cell death in the nonnormal cancerous cells.

The compositions of the present invention may be used as an alternative to surgery, either systemically or parenterally, and optionally in combination with another chemotherapeutic or radiation regimen.

The present invention provides a further method for altering the viability of nonnormal or nonhealthy cells, particularly cancerous cells. More particularly, by employing the compositions described herein, apoptotic or necrotic cell death, or both, is induced in nonnormal or nonhealthy cells preferentially over healthy cells. A composition comprising one or more of the components described previously is allowed to contact one or more of the nonnormal or nonhealthy cells of interest by either systemic or parenteral means. Preferably, at least 50%, even more preferably at least 75%, and most preferably about 90%, of the nonnormal cells in the tissue of interest die by necrotic or apoptic mechanisms, or both. If administration is via a systemic route, preferably the maximum amount of cell death occurs within 90 h. of administration, and more preferably within 24 h. If administration is by intratumoral injection, preferably the maximum amount of cell death is induced within 4 hours, and more preferably within 1–2 h.

The present invention illustrates a selective effect on the viability of nonnormal cells over healthy, normal cells. Preferably less than 50% of the healthy cells of a comparable tissue type and size to the nonnormal tissue die either by a necrotic or apoptotic mechanism, or both; more preferably less than 25%, even more preferably less than 10%, and most preferably less than 1%.

Methods for determining the amount of necrosis or apoptosis are well known in the art. Apoptosis may be measured by, for example, the annexin V-FITC apoptosis detection kit (Oncongene Research Products, CN Biosciences, Inc.). Other known methods to measure apoptosis include (i) the TUNEL flow cytometry assay (terminal deoxynucleotidyl transferase-mediated dUPT nick end-labeling); (ii) laser scanning microscope imaging of propidium iodide fluorescence; (iii) visualization of cell nuclei and DNA with 4'6-diamino-Z-phenylindole staining or bisbenzimide (fluorescent microscopy); (iv) staining of cells with acridine orange or hematoxylin eosin (followed by light microscopy); or (v) DNA fragmentation analysis. Such studies can be complemented by examining the expression of pro- and anti-apoptotic gene products (e.g., Bax, p53, Bcl-2, etc.).

For assaying necrosis, the widely-used trypan blue method is used. While healthy cells and apoptotic cells (including the resulting apoptotic bodies) exclude trypan blue, necrotic cells are permeable to trypan blue and can be visualized by light microscopy.

For the determination of cell proliferation, the MTT assay is used. This colorimetric assay is based on the ability of living cells, but not dead cells, to reduce 3-(4, 5-dimethyl thiazol-2-yl)-2, 5-diphenyltetrazolium bromide. See, Carmichael, J., De Graff, W. G., Gazdar, A. F., Minna, J. D. & Mitchell, J. B. "Evaluation of Tetrazolium-Based Semi-automated Colorimetric Assay: Assessment of Chemosensitivity Testing," *Cancer Res.* 47, 39–942 (1987).

To further evaluate cell death, cells are grown in 12-well plates, and cellular morphology is assessed by microscopic examination after cytologic staining (e.g., with Giemsa). To verify whether cells are alive and able to proliferate, $^3$[H] thymidine is added to the cells and after 1–4 h. of incubation, the incorporation of $^3$[H]thymidine into DNA is determined as described in Masahiro Tomono and Zoltan Kiss, "Ethanol Enhances The Stimulatory Effects of Insulin and Insulin-Like Growth Factor-I on DNA Synthesis in NIH 3T3 Fibroblasts", Biochemical and Biophysical Research Communications, 208(1):63–67 (1995).

The present invention also provides a rapid and efficient method for identifying an effective composition for altering the viability of a variety of nonnormal or nonhealthy cells, particularly cancers and cancer subtypes. The method is comprised of steps wherein a set of variable components that includes at least two, preferably three, and most preferably all four of the components A, B, C, and D is provided for incorporation into a library of test compositions. The test compositions in the library so generated may vary based on the number of components incorporated, the chemical identity of the components incorporated, their concentrations, and the like. The library so generated is then examined to determine if any of the test compositions therein induces a desired biological effect against one or more nonhealthy or nonnormal cell types. Based on the results, the desired composition is selected from among the test compositions in said library. The desired composition may be used, for example, to treat a heterogeneous cancerous tumor, or alternatively to treat a more homogeneous cancerous tumor. The method can be used to generate a preferred composition specifically tailored to be maximally effective in altering the viability of a particular cancer, while exhibiting minimal alteration in the viability of healthy, normal cells. Alternatively, the particular composition may be chosen to be more broadly effective against a range of cancers, while nonetheless remaining minimally toxic to healthy cells.

In one embodiment, a library of test compositions comprising all four components A, B, C, and D is generated. For component A, the investigator is allowed to choose from among PDC, DEDC, D609, or Disulfuram in concentration ranges (representing final concentration) from about 5–250 $\mu$M. For component B, the investigator can choose from among $Zn^{2+}$ or $Cu^{2+}$, in concentration ranges from about 20–500 $\mu$M. For component C, the investigator can choose ethacrynic acid (EA), L-buthionine-S,R-sulfoximine (BSO), diethylmaleate, 2-cyclohexene-1-one, or 1-chloro-2,4-dinitrobenzene (CDNB), in concentration ranges from about 10–300 $\mu$M. For component D, the investigator chooses DMETN in a concentration range of about 3–40 mM.

After preparing the library of such test compositions, the investigator examines each one to determine if it induces a desired biological effect against one or more nonhealthy or nonnormal cell types. In one embodiment, the investigator examines whether apoptosis and/or necrosis are induced in a particular breast cancer cell line, such as MDB-MB-231, human mammary gland epithelial adenocarcinoma, estrogen receptor negative. The investigator further examines the biological effect of the compositions on normal, healthy breast epithelial cells. Means for measuring necrosis and apoptosis are well known in the art, as described previously.

For example, the annexin V-FITC apoptosis detection kit (Oncogene Research Products, CN Biosciences, Inc.) can determine the number of cells that died via an apoptotic mechanism.

After examining the biological effect of the library on the cancerous and healthy cell-lines, the investigator determines the test composition which maximally induces necrosis and/or apoptosis, or both, in the cancerous line, and minimally induces necrosis and/or apoptosis in the healthy, normal cell line.

The compositions and methods of the present invention are effective against a broad array of cancerous tissues and cell-types, including but not limited to breast (both estrogen receptor positive and negative), epidermal, melanomal, colorectal, bladder, cervical, neuroblastomal, prostate, ovarian, endometrial, and placental cancers. The ability of the present compositions to induce a mixture of apoptosis or necrosis, or both, in a broad range of cancerous cell lines, while preferably exhibiting minimal alteration in the viability of healthy cells, is exemplified below.

IV. EXAMPLES

The ability of the compositions to alter the viability of a broad range of cancerous cell types, while inducing less changes in minimally affecting the viability of noncancerous cells, are set forth in detail in Examples 1–24 below.

In Vitro Experiments

Unless otherwise indicated, all cell lines were purchased from the American Type Culture Collection (ATCC). DTCs, EA, DMETN, and $ZnCl_2$, were purchased from Sigma, while all media, L-glu, BSS, and fetal bovine serum were purchased from Gibco. The general recipes for each medium are described in the Gibco catalogue and general recipes for the media indicated in each example.

Determination of Necrosis, Apoptosis, % Cell Death, Morphological Changes, DNA Synthesis and Cell Proliferation Rates.

To determine the effects of the present compositions, cells were grown in the indicated medium in either 12-well plates (to assess morphological changes and measure DNA synthesis); 6-well plates (for determination of apoptosis/necrosis); or 96-well plates (for determination of cellular proliferation by the MTT assay). All media contained 10% fetal bovine serum. In each experiment, the medium was replaced with fresh medium at 2 h. prior to treatment. Treatments were performed with sterile solutions of the compositions (made up either in the respective medium or water) for 1 min.–72 h. In some cases, treatments were done for 1 min., followed by incubation of washed cells for various time periods.

To study apoptosis, annexin-V staining was followed by flow cytometric measurements. Briefly, treated cells were harvested by trypsinization. One million cells for each treatment were washed with phosphate buffered saline (PBS)/1% bovine serum albumin (BSA) followed by ice-cold PBS. After centrifugation at 700 rpm for 8 min., cell pellets were resuspended with 100 $\mu$l of annexin-V binding buffer (10 mM HEPES—NaOH, pH 7.4, 150 mM NaCl, 5 mm KCl, 1 mM $MgCl_2$, 1.8 mM $CaCl_2$) containing 5 $\mu$g/ml propidium iodide and annexin-V-biotin reagent diluted 1:100. The suspension was kept in the dark for 15 min. at room temperature. Cells incubated with annexin-V-biotin were collected by spinning at 700 rpm at 4° C. for 8 min. The pelleted cells were further incubated with streptavidin-FITC reagent (fluorescein isothiocyanate) at a dilution of 1:100 for 15 min. at room temperature in the dark. After incubation, 400 $\mu$l of the annexin-V-binding buffer was added to each sample before flow cytometric analysis. The threshold for an event in cytometric analysis was kept at 5%. More than $4 \times 10^6$ events were counted for each treatment. Flow cytometry analysis was performed with a Beckton Dickinson FACS instrument.

The annexin V-biotin kit was purchased from Trevigen, Gaithersburg, Md.; the streptavidin-FITC reagent from Santa Cruz Biotechnology, Santa Cruz, Calif. For some studies an "annexin-V-FITC apoptosis detection kit" was purchased from Oncogene Research Products, CN Biosciences.

Photography of Cells

Cells were photographed with a Polaroid camera, or with a conventional camera with the prints made via conventional methods.

Example 1

SK-MEL-24, Human Melanoma

Cells were cultured in minimum essential medium according to Eagle, with 2 mM L-glutamine and Earle's BSS balanced salt solution containing 10% fetal bovine serum; the medium was changed 2 h. prior to treatment. Cells were treated with a composition comprising 50 $\mu$M PDC, 120 $\mu$M Zn (as zinc chloride in all examples), 60 $\mu$M EA, and 3 mM DMETN for 1 minute, with a medium change and incubation for 4 hours, or continuously for 30 min. For DNA synthesis experiments, cells were incubated with [$^3$H]-thymidine (1 $\mu$Ci/ml) (New England Nuclear) between 30–40 mins. of treatment; for cell proliferation experiments, cells were trypsinized after treatment, re-plated, and viable cells counted 1 week later.

Figure 7A:
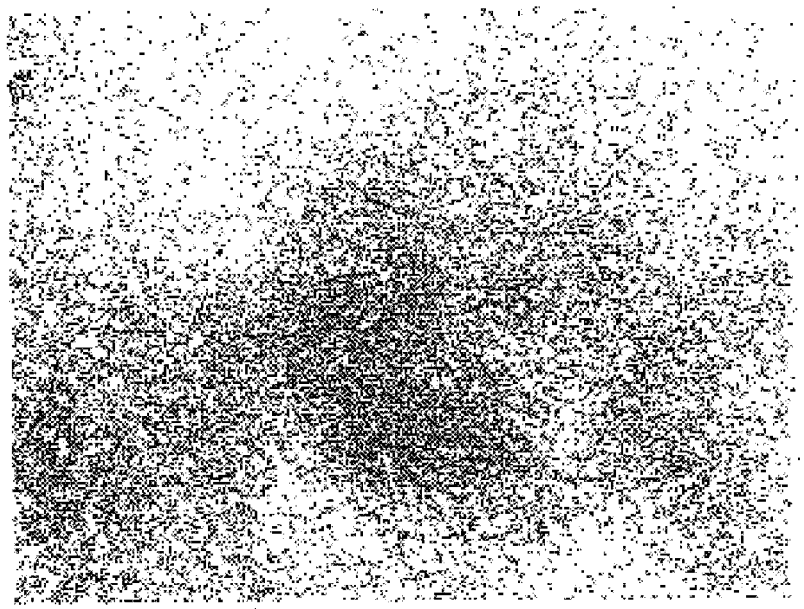
FIGS. 7a and 7b. SK-MEL-24 human melanoma, untreated (FIG. 7a) and treated with a composition comprising PDC (50 $\mu$M), zinc (120 $\mu$M), ethacrynic acid (60 $\mu$M), and dimethylethanolamine (3 mM) for 1 minute, with medium change and incubation for 4 hours (FIG. 7b). After treatment, about 100% of cells were killed based on cellular morphology changes (rounding, removal from well-plate surface), and DNA and cell proliferation measurements.
Figure 7B:
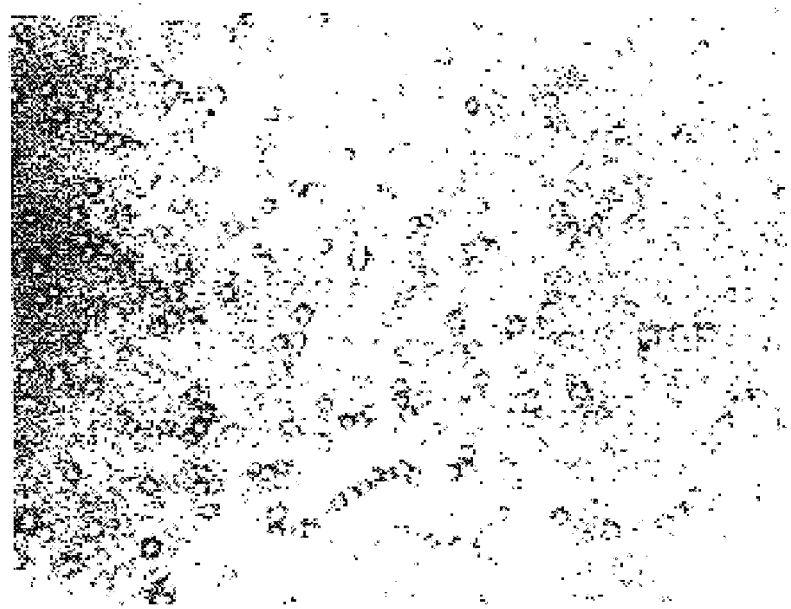

After 30 mins. of treatment, the composition killed about 100% of cells, based on morphology, DNA synthesis, and cell proliferation measurements. See FIGS. 7a and 7b. A composition of PDC and Zn alone at the concentrations above killed about 100% of the cells after 60–90 mins. of treatment.

After 1 min. of treatment, followed by four hours of incubation in fresh medium, the composition killed about 100% of the cells, based on the morphology, DNA synthesis, and cell proliferation measurements. A composition of PDC and Zn alone at the concentrations above killed about 60–65% of the cells.

Example 2

SK-MEL-28, Human Melanoma

Cells were cultured in minimum essential medium Eagle with 2 mM L-glutamine and Earle's BSS containing 10% fetal bovine serum; the medium was changed 2 h. prior to treatment. Cells were treated continuously with a composition comprising 50 $\mu$M PDC, 120 $\mu$M Zn, 60 $\mu$M EA, and 3 mM DMETN for 1 min., with a medium change and treated for 4 h., or continuously for 30 min. For DNA synthesis experiments, cells were incubated with [$^3$H]-thymidine (1 $\mu$Ci/ml) between 30–40 mins. of treatment; for cell proliferation experiments, cells were trypsinized after treatment, re-plated, and viable cells counted 1 week later.

Figure 4A:
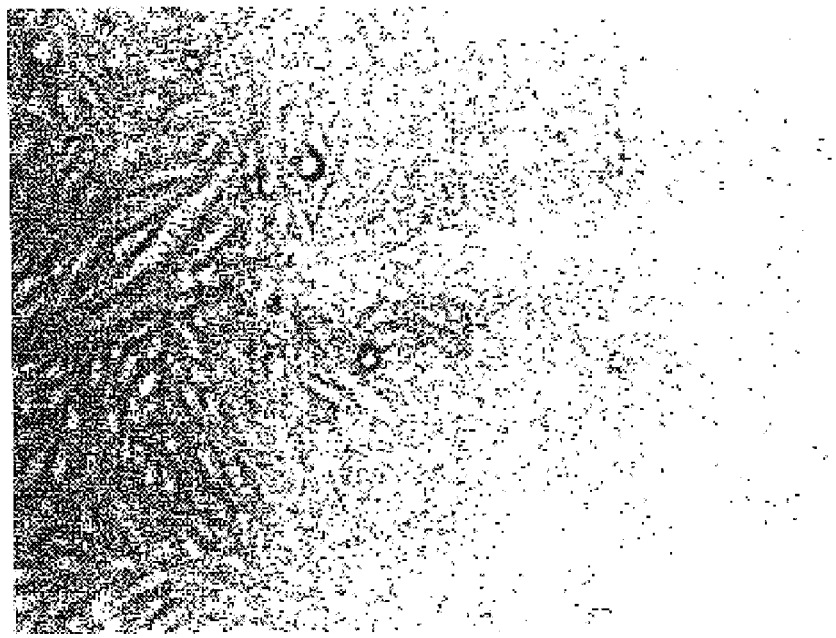
FIGS. 4a and 4b. SK-MEL-28 human melanoma, untreated (FIG. 4a) and treated with a composition comprising PDC (50 EM), zinc (120 $\mu$M), ethacrynic acid (60 $\mu$M) and dimethylethanolamine (3 mM) for 30 minutes (FIG. 4b). After 30 min. of treatment, about 100% of the cells were dead, based on cell morphology (rounding, removal from well-plate surface), DNA synthesis and cell proliferation measurements. When treated cells were washed after 30 min. of treatment with fresh medium and incubated in fresh medium, no viable cells were found after 3 days.
Figure 4B:
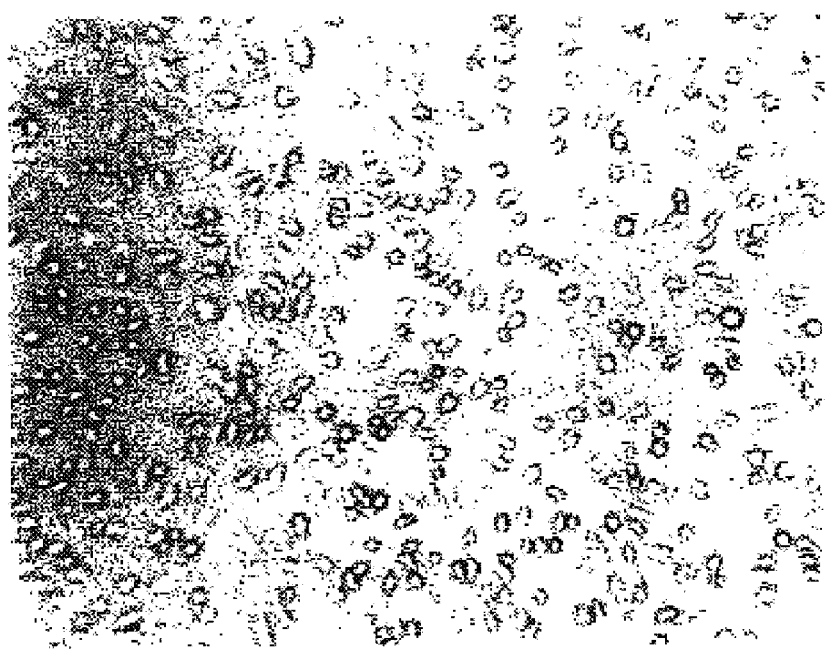

After 30 mins. of treatment, the composition killed about 100% of cells, based on the morphology, DNA synthesis, and cell proliferation measurements. See FIGS. 4a and 4b. A composition of PDC and Zn alone at the concentrations above killed about 100% of the cells after 60–90 mins. of treatment.

After 1 min. of treatment, followed by four hours of incubation in fresh medium, the composition killed about 100% of the cells, based on the morphology, DNA synthesis, and cell proliferation measurements. Compositions (at the above concentrations) of PDC and Zn; PDC, Zn, and EA; or PDC, Zn, and DMETN killed about 70–85% of cells after 1 min. of treatment followed by four hours of incubation in fresh medium.

Example 3

SK-1058, Normal Human Skin Fibroblast

Cells were cultured in minimum essential medium Eagle with 2 mM L-glutamine and Earle's BSS containing 10% fetal bovine serum; the medium was changed 2 h. prior to treatment. Cells were treated continuously with a composition comprising 50 $\mu$M PDC, 120 $\mu$M Zn, 60 $\mu$M EA, and 3 mM DMETN continuously for 25 min. For DNA synthesis experiments, cells were incubated with [$^3$H]-thymidine (1 $\mu\mu$Ci/ml) between 25–35 mins. of treatment; for cell proliferation experiments, cells were trypsinized after treatment, re-plated, and viable cells counted 1 week later.

Figure 3A:
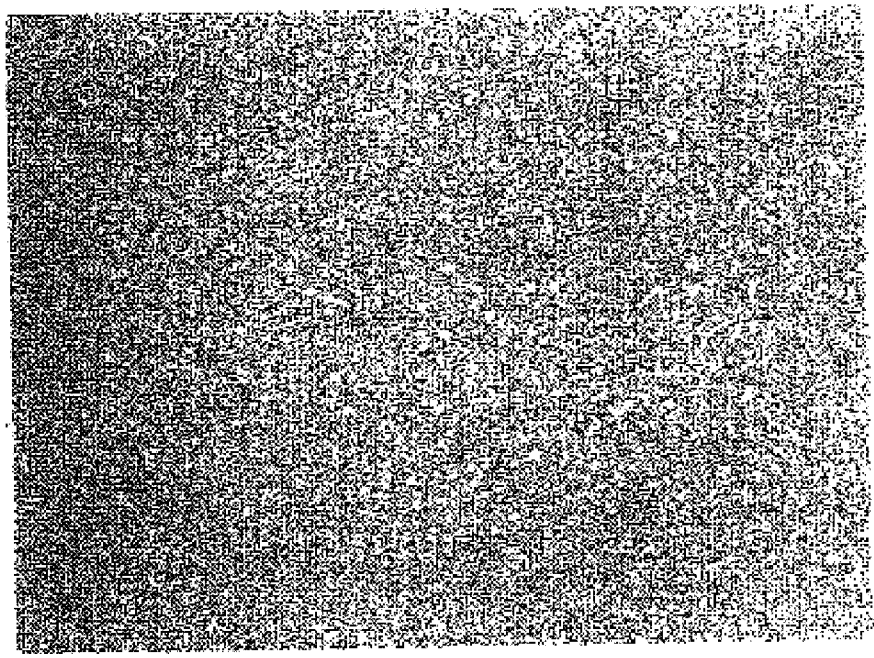
FIGS. 3a and 3b. SK-1058 normal human skin fibroblast cells, untreated (FIG. 3a) and treated with a composition comprising PDC (25 $\mu$M), zinc (60 $\mu$M), ethacrynic acid (60 $\mu$M) and dimethylethanolamine (3 mM) for 25 minutes (FIG. 3b). Cellular morphology is unchanged in these normal skin fibroblast cells after treatment.
Figure 3B:
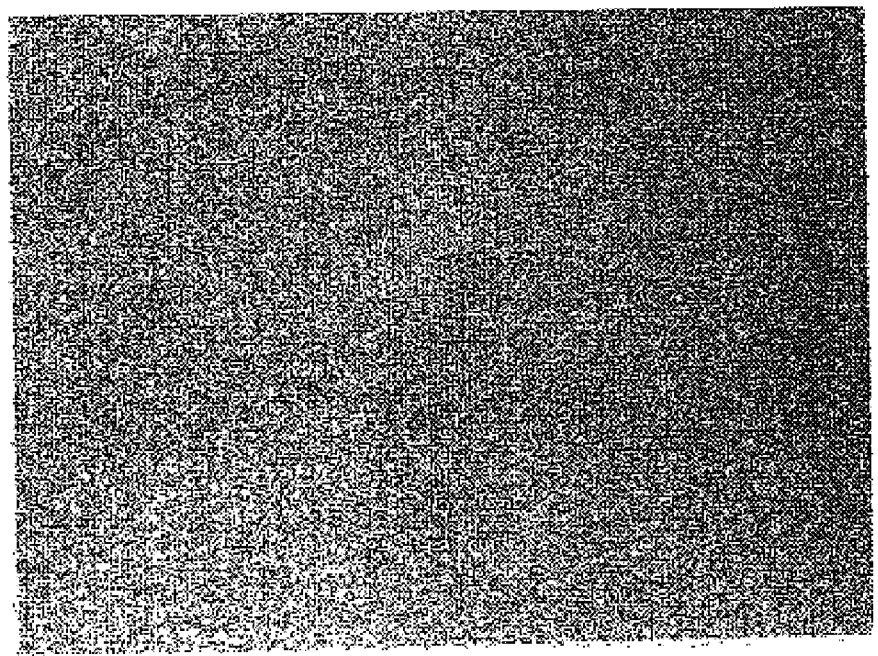

After 25 min., the composition did not change cell morphology, but decreased DNA synthesis and cell proliferation by about 10% and about 60%, respectively. See FIGS. 3a and 3b. While DNA synthesis is not affected greatly, the cell proliferation experiments indicate that a shorter exposure or lower dosage might be desired to minimize altering the viability of normal fibroblasts.

Also note that SK-MEL-28 is independent of SK-MEL-24, but the 2 cell lines responded similarly to the compositions described. Intratumoral or topical application of the compositions to skin melanomas, which are known to be heterogenous, is expected to be effective in treating melanomas, as is further indicated by the data below on human melanoma xenografts.

Example 4

A431, Human Epidermoid Carcinoma

Cells were cultured in minimum essential medium Eagle with 2 mM L-glutamine and Earle's BSS containing 10% fetal bovine serum; the medium was changed 2 hour prior to treatment. Cells were treated continuously with a composition comprising 25 $\mu$M PDC, 60 $\mu$M Zn, 40 $\mu$M EA, and 3 mM DMETN continuously for 60 min. For DNA synthesis experiments, cells were incubated with [$^3$H]-thymidine (1 $\mu$Ci/ml) between 60–70 mins. of treatment; for cell proliferation experiments, cells were trypsinized after treatment, re-plated, and viable cells counted 1 week later.

After 60 min. the composition killed about 100% of the cells, based on morphology and DNA synthesis and cell proliferation measurements. A composition of PDC and Zn, at the above concentrations, killed about 60–70% of the cells.

Example 5

MDA-MB-231, Human Mammary Gland (Epithelial) Adenocarcinoma, Estrogen Receptor Negative Cells were cultured in Leibovitz's L-15 cell culture medium (Gibco) and 10% fetal bovine serum; the medium was changed 6 h. prior to treatment. Cells were incubated continuously with a composition comprising 25 $\mu$M PDC, 60 $\mu$M Zn, 60 $\mu$M EA, and 3 mM DMETN for 40 min. For DNA synthesis experiments, cells were incubated with [$^3$H]-thymidine (1 $\mu$Ci/ml) between 40–50 mins. of treatment; for cell proliferation experiments, cells were trypsinized after treatment, re-plated, and viable cells counted 1 week later.

Figure 6A:
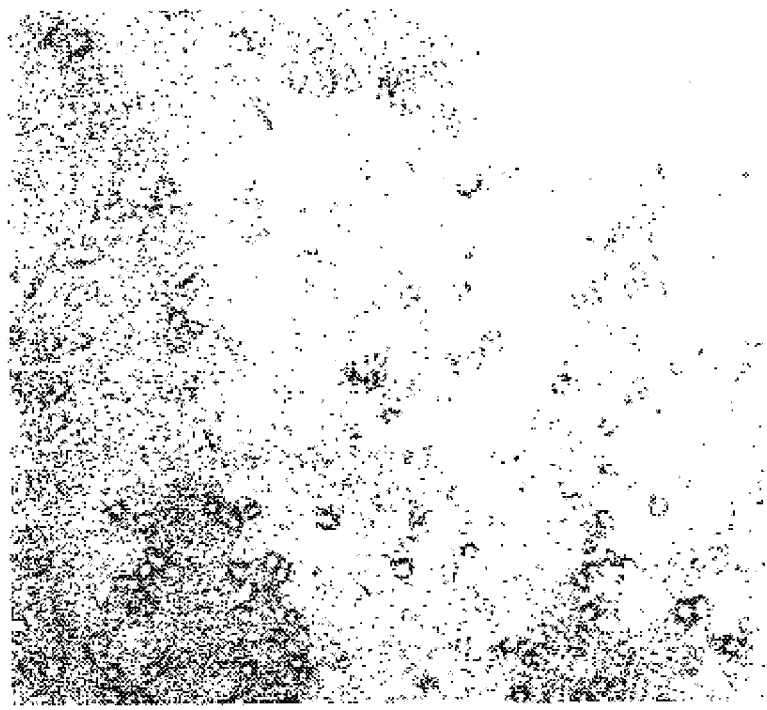
FIGS. 6a and 6b. MDA-MB-231 human mammary gland epithelial adenocarcinoma, untreated (FIG. 6a) and treated with a composition comprising PDC (25 $\mu$M), zinc (60 $\mu$M), ethacrynic acid (60 $\mu$M), and dimethylethanolamine (3 mM) for 40 minutes (FIG. 6b). After 40 min. of treatment, about 100% of the cells were killed based on cellular morphology changes (rounding, removal from well-plate surface), and DNA and cell proliferation measurements.
Figure 6B:
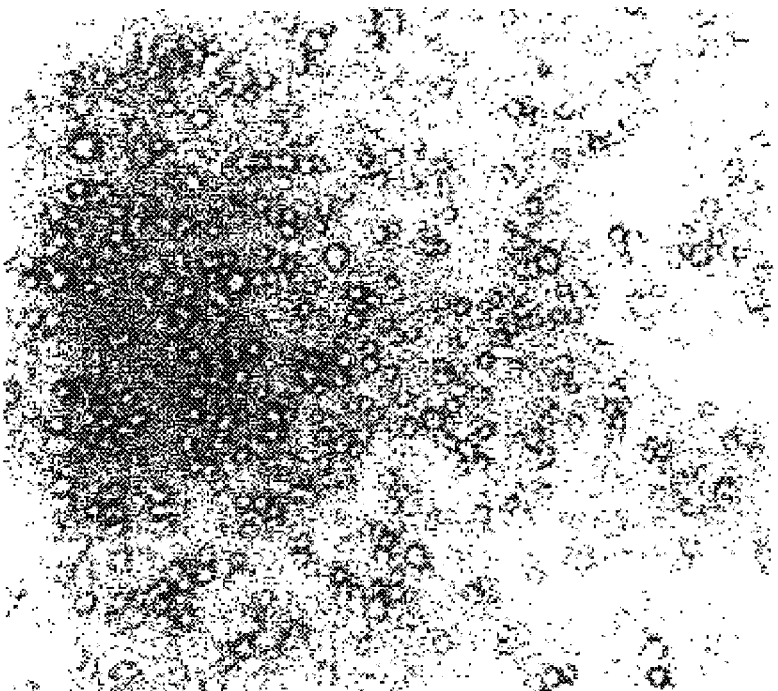

After 40 min. of treatment, the composition killed about 100% of cells based on cell morphology, DNA synthesis, and cell proliferation experiments. See FIG. 6. A composition of EA alone, at the concentration above, killed about 70% of the cells after 40 min., and about 100% of the cells after 3 h.

Compositions comprising D609, DEDC, and disulfuram were as effective as compositions comprising PDC under the same conditions.

When the same cells were treated for 5 min. with a replacement of fresh medium and incubation for 4 hours, the composition killed about 100% of the cells. A composition of EA, PDC, and Zn at the above concentrations killed about 80–85% of the cells under the same conditions; a composition of PDC, Zn, and DMETN under the same conditions killed about 70–75% of the cells.

When the same cells were treated for 75 h. with a composition comprising 10 $\mu$M EA and 20 $\mu$M PDC, about 100% of the cells were dead, while normal human fibroblasts or untransformed MCF-10A human breast epithelial cells were less affected (10–20% of cells died). These experiments indicate that lower concentrations of the compositions, combined with a longer exposure, result in massive cell death in this line, while healthy, normal cells are less affected.

Example 6

MDA-MB-468, Human Mammary Gland (Epithelial) Adenocarcinoma, Estrogen Receptor Negative Cells were cultured in Leibovitz's L-15 medium and 10% fetal bovine serum; the medium was changed 6 h. prior to treatment. Cells were treated continuously with a composition comprising 25 $\mu$M PDC, 120 $\mu$M Zn, 100 $\mu$M EA, and 3 mM DMETN for 2 h. For DNA synthesis experiments, cells were incubated with [$^3$H]-thymidine (1 $\mu$Ci/ml) between 120–130 mins. of treatment; for cell proliferation experiments, cells were trypsinized after treatment, re-plated, and viable cells counted 1 week later.

After 2 h. of treatment, the above composition, as well as the compositions comprising (EA, PDC, and Zn) and (PDC, Zn, and DMETN) killed about 100% of cells.

After 18 h. of treatment, a composition of 50 $\mu$M EA and 20 $\mu$M PDC killed about 100% of cells. After 75 h., a composition of 10 $\mu$M EA and 20 $\mu$M PDC killed about 100% of cells.

Compositions comprising D609 and DEDC were as effective as those comprising PDC in the above experiments.

Example 7

T-47D, Human Mammary Gland (Epithelial) Ductal Carcinoma, Estrogen Receptor Positive Cells were cultured in modified RPMI 1640 cell culture medium (see Gibco Catalogue), with 2 mM L-glutamine, 10 mM Hepes, 1 mM sodium pyruvate, 4.5 g/L glucose, 1.5 g/L sodium bicarbonate, 0.2 I.U. bovine insulin/ml, and 10% fetal bovine serum; the medium was changed 6 h. prior to treatment. Cells were treated continuously with a composition comprising 50 $\mu$M PDC, 120 $\mu$M Zn, 100 $\mu$M EA, and 3 mM DMETN for 2 h. For DNA synthesis experiments, cells were incubated with [$^3$H]-thymidine (1 µCi/ml) between 120–130 mins. of treatment; for cell proliferation experiments, cells were trypsinized after treatment, replated, and viable cells counted 1 week later.

Figure 9A:
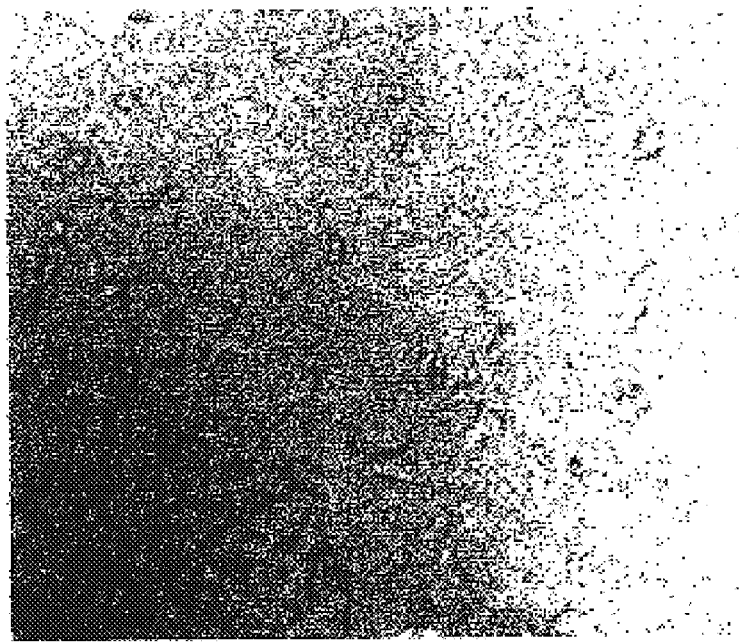
FIGS. 9a and 9b. T-47D; human mammary gland (epithelial) ductal carcinoma, estrogen receptor positive, untreated (FIG. 9a) and treated with a composition comprising EA (100 $\mu$M) (FIG. 9b). After 2 h. of treatment, about 100% of cells were killed based on morphology as well DNA synthesis and cell proliferation measurements.
Figure 9B:

After 2 h., the composition killed about 100% of cells, based on morphology and DNA synthesis and cell proliferation experiments. Compositions of EA alone or of PDC and Zn at the above concentrations also killed about 100% of cells. See FIGS. 9a and 9b.

After 36 h. of incubation, a composition comprising 50 µM EA and 20 µM PDC killed about 100% of cells. After 75 h., a composition comprising 20 µM EA and 20 µM PDC killed about 100% of cells.

Compositions comprising D609 and DEDC were as effective as those comprising PDC in the above experiments.

Example 8

ZR-75-1, human mammary gland (epithelial) ductal carcinoma, ascites, estrogen receptor positive. Cells were cultured in modified RPMI 1640 medium with 2 mM L-glutamine, 10 mM Hepes, 1 mM sodium pyruvate, 4.5 g/L glucose, 1.5 g/L sodium bicarbonate, 0.2 I.U. bovine insulin/ml, and 10% fetal bovine serum; the medium was changed 6 h. prior to treatment. Cells were treated continuously with a composition comprising 50 µM PDC, 120 µM Zn, 100 µM EA, and 3 mM DMETN for 2 h. For DNA synthesis experiments, cells were incubated with [$^3$H]-thymidine (1 µCi/ml) between 120–130 mins. of treatment; for cell proliferation experiments, cells were trypsinized after treatment, re-plated, and viable cells counted 1 week later.

After 2 h., the composition killed about 100% of cells, based on morphology and DNA synthesis and cell proliferation experiments. Compositions of EA alone or of PDC and Zn at the above concentrations also killed about 100% of cells.

After 16 h. of incubation, a composition comprising 50 µM EA and 20 µM PDC killed 100% of cells. After 75 h., a composition comprising 20 µM EA and 20 µM PDC killed 100% of cells.

If treatments were only for 5 min., followed by incubation for 2 h. in fresh medium, only the composition comprising all four components PDC, EA, DMETN, and Zn killed about 100% of cells.

Compositions comprising D609 and DEDC were as effective as those comprising PDC in the above experiments.

Example 9

MCF-7/MDR1, Multidrug Resistant Estrogen Receptor-Negative Subline of the MCF-7 Human Mammary Gland Estrogen Receptor Positive Adenocarcinoma Line Note: the source of this cell line was Dr. Kenneth Cowan, National Institutes of Health, Bethesda, Md. Cells were cultured in Dulbecco's modified Eagles' cell culture medium (see Gibco catalogue) containing 2 mM L-glutamine and 10% fetal calf serum. The medium was changed 6 h. prior to treatment. Cells were treated continuously with a composition comprising 25 µM PDC, 60 µM Zn, 60 µM EA, and 3 mM DMETN for 160 min. For DNA synthesis experiments, cells were treated with [$^3$H]-thymidine (1 µCi/ml) between 160–170 mins. of treatment; for cell proliferation experiments, cells were trypsinized after treatment, re-plated, and viable cells counted 1 week later.

Figure 8A:
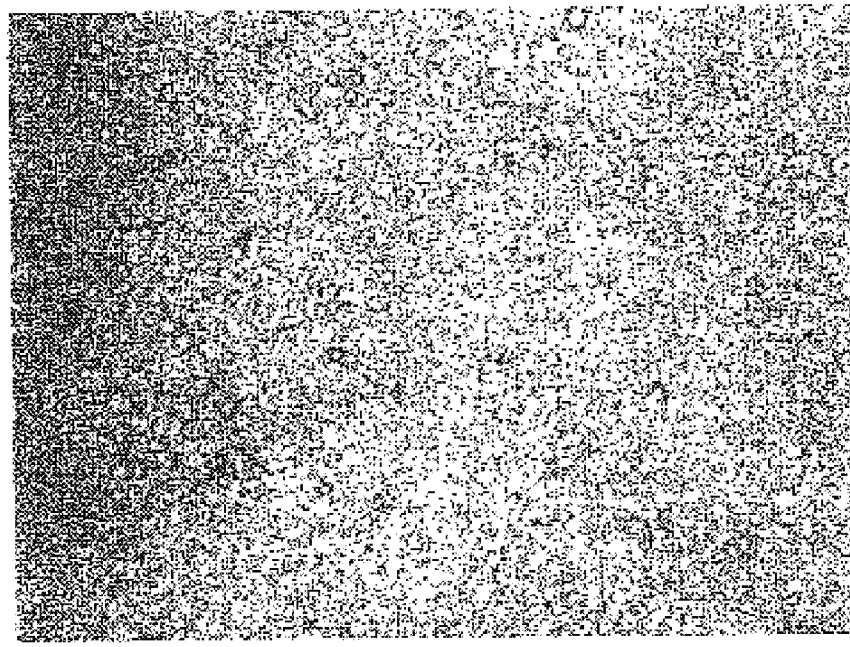
FIGS. 8a and 8b. MCF-7/MDR1 multidrug resistant, estrogen receptor-negative subline of MCF-7 human mammary gland estrogen receptor positive adenocarcinoma line, untreated (FIG. 8a), and treated with a composition comprising PDC (25 $\mu$M), zinc (60 $\mu$M), ethacrynic acid (60 $\mu$M), and dimethylethanolamine (3 mM) for 160 minutes (FIG. 8b). After 160 min. of treatment, about 100% of the cells are killed based on cell morphology changes (rounding, removal from well-plate surface), and DNA synthesis and cell proliferation rates.
Figure 8B:
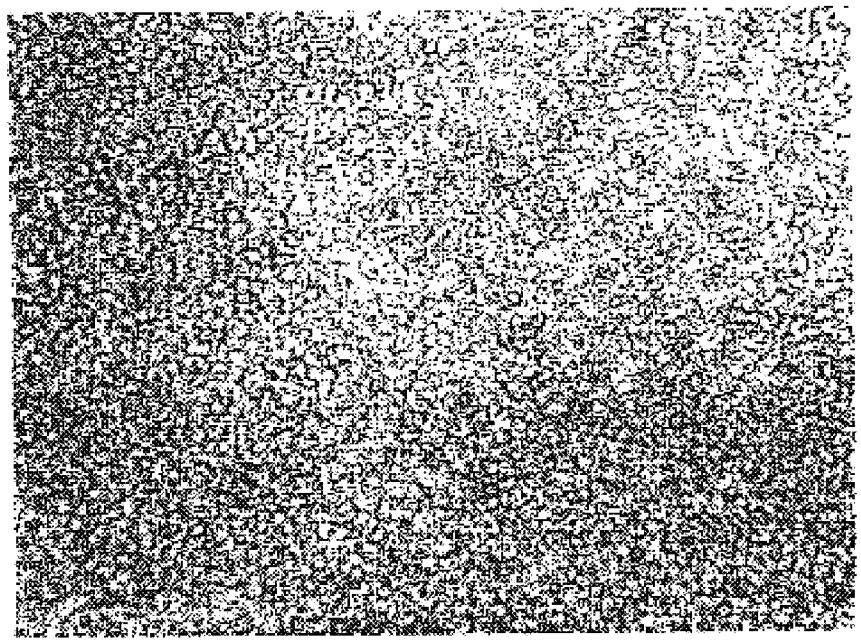

After 160 min., the composition killed about 100% of cells. See FIGS. 8a and 8b. A composition comprising EA, PDC, and Zn at the above concentrations killed about 90% of cells.

Example 10

MCF-10A, Untransformed (Control) Breast Epithelial Cells

Cells were cultured in a 1:1 mixture of Dulbecco's modified Eagle's medium and Ham's F12 cell culture medium (for composition see Gibco catalogue) with 20 ng/ml epidermal growth factor, 100 ng/ml cholera toxin, 0.01 mg/ml insulin, 500 ng/ml hydrocortisone, and 5% horse serum. The medium was changed for fresh medium 6 h. prior to treatment. Cells were treated with a composition comprising 25 µM PDC, 60 µM Zn, 40 µM EA, and 3 mM DMETN continuously for 4 h. For DNA synthesis experiments, cells were incubated with [$^3$H]-thymidine (1 µCi/ml) between 240–250 mins. of treatment; for cell proliferation experiments, cells were trypsinized after treatment, re-plated, and viable cells counted 1 week later.

Figure 5A:
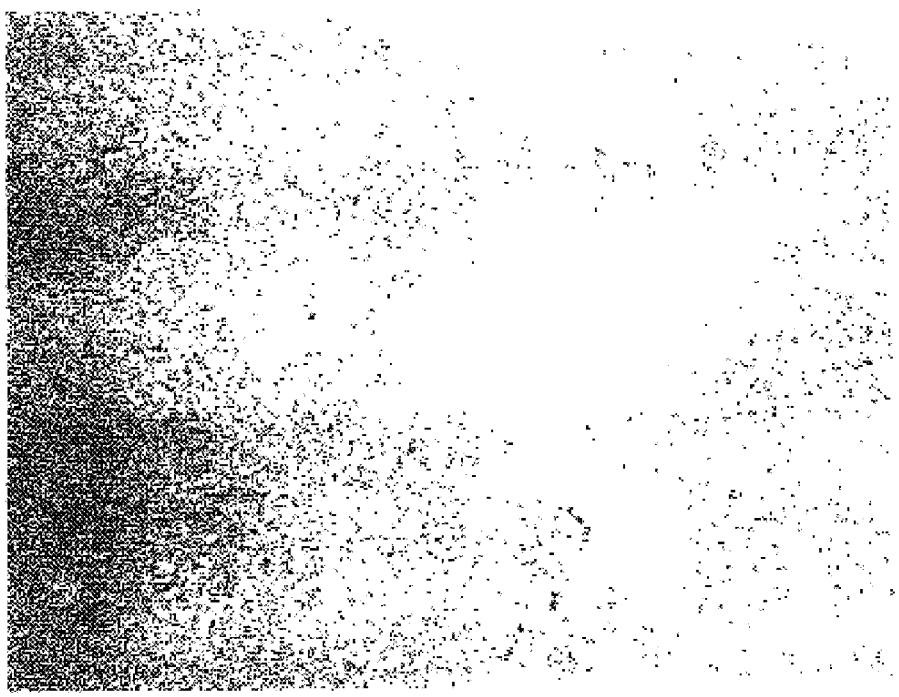
FIGS. 5a and 5b. MCF-10A untransformed (control) human breast epithelial cells, untreated (FIG. 5a) and treated with a composition comprising PDC (25 $\mu$M), zinc (60 $\mu$M), ethacrynic acid (40 $\mu$M) and dimethylethanolamine (3 mM) for 4 hours (FIG. 5b). Note that even after 4 hours of treatment, there is only minimal change in cellular morphology (rounding, removal from well-plate surface); DNA synthesis and cell proliferation rates were only affected modestly (about 20–30% reduction).
Figure 5B:
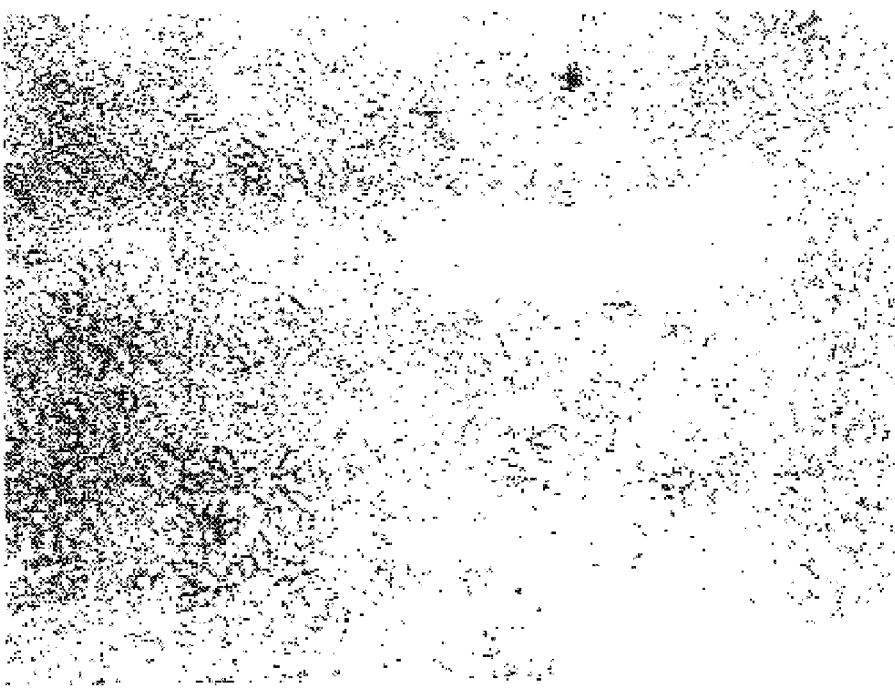

Even after 4 h. of continuous treatment, DNA synthesis and cell proliferation were reduced by only about 20–30%, indicating that the composition is significantly less toxic to untransformed breast cells as compared to breast cancer cells. See FIGS. 5a and 5b.

After 75 h. continuous treatment with a composition of 20 µM EA and 20 µM PDC, viability decreased by about 20%.

Example 11

HT-29, Human Colorectal Adenocarcinoma, Epithelial

Cells were cultured in McCoy's 5a cell culture medium (see Gibco catalogue) with 1.5 mM L-glutamine containing 1.5 g/L sodium bicarbonate and 10% fetal bovine serum. The medium was changed 2 h. prior to treatment. Cells were treated with a composition comprising 25 µM PDC, 30 µM Zn, 40 µM EA, and 3 mM DMETN continuously for 20 min. For DNA synthesis experiments, cells were incubated with [$^3$H]-thymidine (1 µCi/ml) for 20–30 mins. of treatment; for cell proliferation experiments, cells were trypsinized after treatment, re-plated, and viable cells counted 1 week later.

Figure 11A:
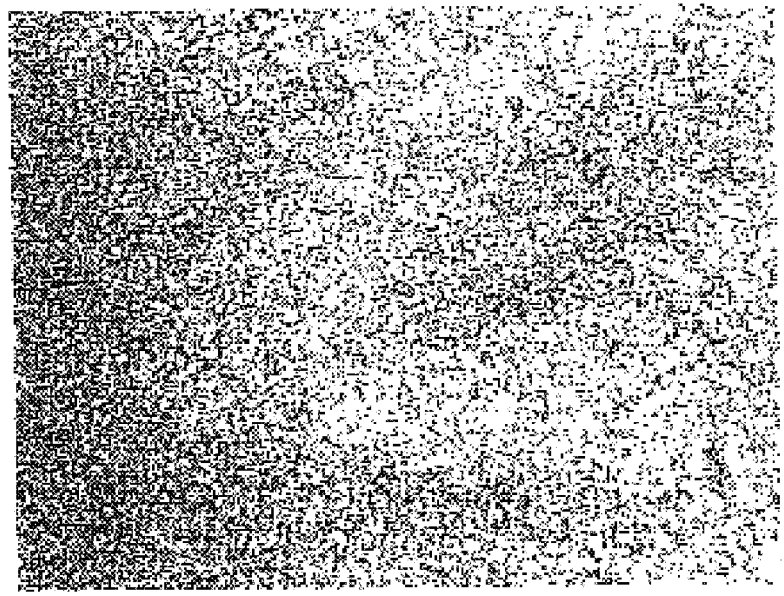
FIGS. 11a and 11b. HT-29, human colorectal adenocarcinoma, epithelial, untreated (FIG. 11a) and treated with a composition comprising PDC (25 $\mu$M), zinc (30 $\mu$M), EA (40 $\mu$M) and DMETN (3 mM) (FIG. 11b). After 20 mins., about 100% of cells were dead based on DNA synthesis and cell proliferation data.
Figure 11B:
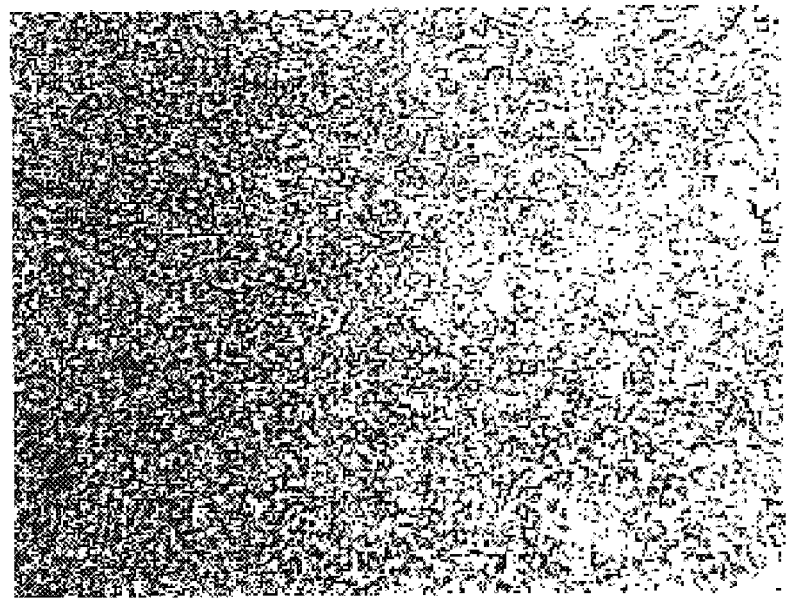

After 20 min., the composition killed about 100% of cells. See FIGS. 11a and 11b. A composition of PDC and Zn at the above concentrations killed about 60–70% of cells.

Example 12

Caco-2, Human Colorectal Adenocarcinoma, Epithelial

Cells were cultured in Eagle's minimal essential medium with Earle's BSS and 2 mM L-glutamine containing 0.1 mM sodium pyruvate, 0.1 mM nonessential amino acids, 1.5 g/L sodium bicarbonate, and 20% fetal bovine serum. The medium was changed 2 h. prior to treatment. Cells were treated with a composition comprising 50 µM PDC, 120 µM Zn, 100 µM EA, and 3 mM DMETN continuously for 2.5 h. For DNA synthesis experiments, cells were incubated with [$^3$H]-thymidine (1 µCi/ml) between 150–160 mins. of treatment; for cell proliferation experiments, cells were trypsinized after treatment, re-plated, and viable cells counted 1 week later.

After 2.5 h., the composition killed about 100% of cells. A composition of comprising EA, PDC, and Zn at the above concentrations also killed about 100% of cells.

Example 13

A549, Human Lung Carcinoma, Epithelial

Cells were cultured in Kaighn's modification of Ham's F12 medium (F12K) with 2 mM L-glutamine containing 1.5 g/L sodium bicarbonate and 10% fetal bovine serum. The medium was changed 2 h. prior to treatment. Cells were treated with a composition comprising 25 μM PDC, 30 μM Zn, 40 μM EA, and 3 mM DMETN continuously for 160 min. For DNA synthesis experiments, cells were incubated with [$^3$H]-thymidine (1 μCi/ml) for 30–40 mins. after treatment; for cell proliferation experiments, cells were trypsinized after treatment, re-plated, and viable cells counted 1 week later.

Figure 10A:
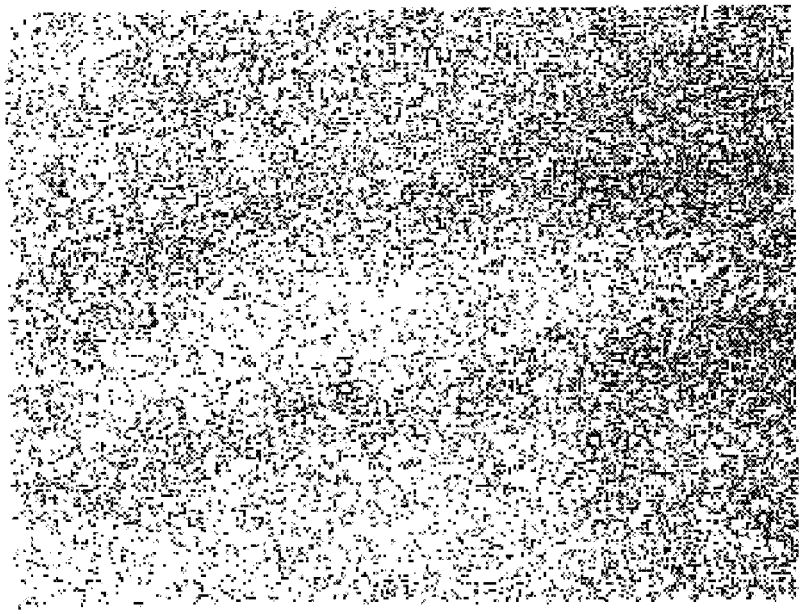
FIGS. 10a and 10b. A549, human lung carcinoma, epithelial, untreated (FIG. 10a) and treated with a composition comprising PDC (25 $\mu$M), zinc (30 $\mu$M), EA (40 $\mu$M) and DMETN (3 mM) (FIG. 10b) for 50 min. After 50 min., about 100% of cells were killed based on DNA synthesis and cell proliferation data.
Figure 10B:
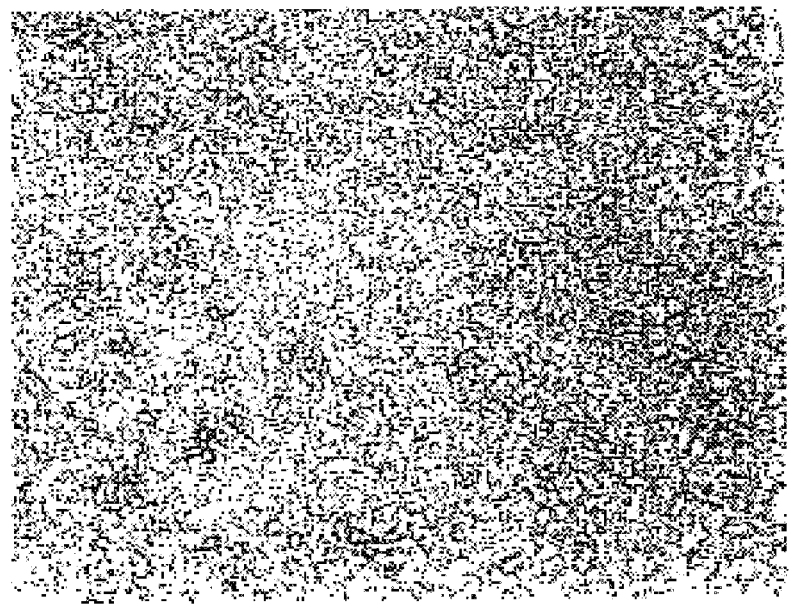

After 30 min., the composition, as well as the composition comprising EA, PDC, and Zn at the above concentrations killed about 100% of cells. See FIGS. 10a and 10b.

Example 14

MCF-7, Human Breast Carcinoma Cells, Estrogen, Receptor Positive

Cells were cultured in Dulbecco's modified Eagle's medium containing 2 mM L-glutamine and 10% fetal calf serum; the medium was changed 2 h prior to treatments. Cells were treated with a composition comprising 50 μM PDC, 120 μm Zn, 80 μM EA and 3 mM DMETN continuously for 2 h. For DNA synthesis experiments, cells were incubated with [$^3$H]-thymidine (1 Ci/ml) between 120–130 min of treatment; for cell proliferation experiments, cells were trypsinized after treatment, re-plated, and viable cells counted 1 week later.

After 2 h, the composition killed about 75–80% of cells, based on morphology, DNA synthesis, and cell proliferation experiments. A composition comprising PDC and Zn at the above concentrations killed only about 15% of cells.

Compositions comprising D609 and DEDC were as effective as those comprising PDC in the above experiments.

Example 15

PC-3, Human Prostate Adenocarcinoma Cells

Cells were cultured in Ham's F12 cell culture medium supplemented with 7% fetal bovine serum; the medium was changed 2 h. prior to treatments. Cells were treated with a composition comprising 50 μM PDC, 120 μM Zn, 80 μM EA, and 3 mM DMETN continuously for 2 h. For DNA synthesis experiments, cells were incubated with [$^3$H] thymidine (1 Ci/ml) between 120–130 min of treatment; for cell proliferation experiments, cells were trypsinized after treatment, re-plated, and viable cells counted 1 week later.

After 2 h, the composition killed about 85% of cells, based on morphology, DNA synthesis, and cell proliferation experiments.

Example 16

Caov-3, Human Ovarian Adenocarcinoma, Papillary

Cells were cultured in Dulbecco's modified Eagle's medium containing 4 mM L-glutamine. 1.5 g/L sodium bicarbonate, 4.5 g/L glucose, 1 mM sodium pyruvate and 10% fetal bovine serum; the medium was changed 2 h prior to treatments. Cells were treated with a composition comprising 50 μM PDC and 50 μM Zn continuously for 90 min. For DNA synthesis experiments, cells were incubated with [$^3$H]-thymidine (1 μCi/ml) between 90–100 min of treatment; for cell proliferation experiments, cells were trypsinized after treatment, re-plated, and viable cells counted 1 week later.

After 2 h., the above 2-component composition killed about 100% of cells, based on morphology, DNA synthesis, and cell proliferation experiments.

Example 17

3A-SubE, Human Transformed Placenta Trophoblast Cells

Cells were cultured in Eagle's minimum essential medium with 0.1 mM non-essential amino acids and 10% fetal bovine serum; the medium was changed 2 h prior to treatments. Cells were treated with a composition comprising 20 μM EA and 20 μM PDC continuously for 48 h. For DNA synthesis experiments, cells were incubated with [$3_H$]-thymidine (1 μCi/ml) for 1 h. at the 48–49 h.; for cell proliferation experiments, cells were trypsinized after treatment, re-plated, and viable cells counted 1 week later.

After 48 h., the above 2-component composition killed about 100% of cells, based on morphology, DNA synthesis, and cell proliferation experiments.

Example 18

AN3; Human, Endometrial Adenocarconoma

Cells were cultured in Eagle's minimum essential medium supplemented with 0.1 mM non-essential amino acids and 10% fetal bovine serum; the medium was changed 2 h. prior to treatments. Cells were treated with a composition comprising 10 μM EA and 20 μM PDC continuously for 36 h. For DNA synthesis experiments, cells were incubated with [$^3$H]-thymidine (1 μCi/ml) for 1 h. at the 36–37 h.; for cell proliferation experiments, cells were trypsinized after treatment, re-plated, and viable cells counted 1 week later.

After 36 h., the above 2-component composition killed about 100% of cells, based on morphology, DNA synthesis, and cell proliferation experiments.

Examples 19 and 20

In Vivo Tumor Transplant Experiments with Mouse C-26 Colon Cancers and Mouse MXT Mammary Cancers Rodent colon-26 (C-26) cancer cells, originally obtained from SRI, Birmingham, Ala., were maintained in Balb/c inbred mice by serial passage in vivo. Rodent MXT mammary carcinoma cells were obtained from the Mason Research Institute (USA) and maintained in BDF1 female mice by serial passage in vivo. Tumor fragments (200–500 mg) were transplanted subcutaneously into the intrascapular region of immunosuppressed CBA/Ca mice. After 7 days of transplantation, animals were anaesthetized and treated (single treatment of a composition comprising PDC (100 μM), zinc (300 μM), EA (200 μM), and DMETN (6 mM)), with 0.3 ml/tumor/mouse equally distributed among six injection sites (i.e., 50 μl/injection site). Biopsies were taken after 2 h. and 4 h. of treatments, followed by cytological examination. The four components were in the following concentration ranges expressed as μg /cm$^3$ tumor volume; PDC, 0.3–10; EA, 1–30; zinc, 0.5–20; DMETN, 10–250. The spots were chosen to provide even coverage of the whole tumor. Exactly 4 hours after injection, 2 samples from each treated tumor and from control tumors treated with 50 ul of 0.9 M NaCl were taken from sites located between two adjacent injection sites. The samples were collected on glass slides and stained with May Grunwald-Giemsa. The experiment was repeated 5–10 times for each tumor type, with at least 2 samples taken for analysis from each treated tumor.

In each tumor, at least 90% of the cells were dead after treatment with the composition described, as indicated by cellular morphology, lysis, membrane blebbing, chromatin condensation, and the appearance of apoptotic bodies. Approximately 60–80% of the cells appeared to die via an apoptotic mechanism. See, FIGS. 1a, 1b, 2a and 2b.

Other compositions were also evaluated on the above mouse tumor transplants. 5–10 tumors were treated with each of the 9 compositions below to evaluate their effects. The compositions were as follows:

1. PDC 12.5 $\mu$M and zinc 37.2 $\mu$M.
2. PDC 25 $\mu$M and zinc 75 $\mu$M.
3. PDC 50.0 $\mu$M and zinc 150.0 $\mu$M.
4. EA 25 $\mu$M and DMETN 1.5 mM.
5. EA 50 $\mu$M and DMETN 3.0 mM.
6. EA 100 $\mu$M and DMETN 6.0 mM.
7. PDC 12.5 $\mu$M and zinc 37.2 $\mu$M and EA 25 $\mu$M and DMETN 1.5 mM.
8. PDC 25 $\mu$M and zinc 75 $\mu$M and EA 50 $\mu$M and DMETN 3.0 mM.
9. PDC 50 $\mu$M and zinc 150 $\mu$M and EA 100 $\mu$M and DMETN 6.0 mM.

Preliminary experiments had indicated that none of the compounds alone had any detectable effects. Compositions 4–6 had only slight apoptosis or necrosis inducing effects.

Examples 21 and 22

In Vivo HT-29 Human Colon Carcinoma and HT-168 Human Melanoma Mouse Xenografts

The HT-29 human colon carcinoma cell line was obtained from the Biological Testing Branch of the National Cancer Institute, Baltimore Md. The HT-168 human melanoma cell line was from the Institute of Pathology and Experimental Cancer Research, Semmelweis Medical University, Budapest, Hungary. Xenografts were established in artificially or genetically immunodeficient (nude) mice. Immunosuppression in CBA/Ca mice was carried out by thymectomy, whole body irradiation (9.5 Gy) and bone marrow transplantation. The humoral and cellular immune response of the artificially immunosuppressed mice was tested by the plaque-forming cell assay and rosette-forming cell assay.

An optimal fragment (200–300 mg) of the tumor was transplanted subcutaneously. After 25 days, the animals were anesthetized by using Napentobarbital (nembutal) i.p., at a dose of 20 mg/kg, shortly before treatment. Fifty microliter aliquots/site of the compositions were injected into the tumor at six different loci, for a total injected volume of 300 microliters. Biopsy was taken from the tumors by aspiration 2 h. or 4 h. after treatment, followed by cytology. After pelleting the cells by short centrifugation, viability was evaluated by the widely used Trypan-blue exclusion. For the evaluation of the ratio of apoptotic cells, cytological smears were stained with May Grunwald-Giemsa. Apoptotic cells were identified on the basis of chromatin condensation, apoptotic bodies, surface blebs, and vacuolization of tumor cells. For Western Blot analysis of p53, Bcl-2, and Bax protein levels, the corresponding commercial antibodies (Santa Cruz Biotechnology, Santa Cruz, Calif.) were used.

For each treatment, 5–10 animals, each carrying 1 tumor, were used. The compositions employed for treatment were as follows:

1. PDC 12.5 $\mu$M and zinc 37.2 $\mu$M.
2. PDC 25 $\mu$M and zinc 75 $\mu$M.
3. PDC 50.0 $\mu$M and zinc 150.0 $\mu$M.
4. EA 25 $\mu$M and DMETN 1.5 mM.
5. EA 50 $\mu$M and DMETN 3.0 mM.
6. EA 100 $\mu$M and DMETN 6.0 mM.
7. PDC 12.5 $\mu$M and zinc 37.2 $\mu$M and EA 25 $\mu$M and DMETN 1.5 mM.
8. PDC 25 $\mu$M and zinc 75 $\mu$M and EA 50 $\mu$M and DMETN 3.0 mM.
9. PDC 50 $\mu$M and zinc 150 $\mu$M and EA 100 $\mu$M and DMETN 6.0 mM.

Preliminary experiments had indicated that none of the compounds alone had any detectable effects. Similarly, compositions comprising PDC and DMETN; zinc and EA; and zinc and DMETN were ineffective. However, after 4 h. of treatment with a composition comprising PDC 50 $\mu$M and zinc 150 $\mu$M, approximately 100% of cells in HT-29 derived tumors were killed by a mixture of apoptotic and necrotic mechanisms. Approximately 64% of cells in HT-168 derived tumors were killed by a mixture of apoptotic and necrotic mechanisms with the same composition. Addition of EA and DMETN to the composition caused an increase of 30% in the killing of HT-168 tumor cells. Approximately 80% of the cells treated with the indicated compositions died via the apoptotic mechanism.

In addition, no viable cells were found after washing and incubation in fresh medium for 3 days from cell cultures derived from HT-168 tumors treated with the composition comprising PDC, zinc, EA, and DMETN.

Example 23

Western Blot Analysis of Apoptotic Gene Product Expression in Cancer Cells

The oncogene Bcl-2 protein protects cells from apoptosis, whereas its homolog Bax functions to kill the cells. (See J. M. Adams, S. Cory, "Life or Death decisions by Bcl-2 protein Family", Trends in Biochem Sci. 26:61–66 (2001).) High Bax and low Bcl-2 levels promote apoptosis. Another important regulator of cell viability is p53; increased expression of p53 results in inactivation of Bcl-2 and up-regulation of Bax, leading to apoptosis. (See, A. Thomas, T. Giesler, and E. White "p53 mediates Bcl-2 phosphorylation and apoptosis via activation of the Cdc42/JNK1 pathway", Oncogene 19:5259–69 (2000) and references therein.)

For Western blot analysis of p53, Bcl-2, and Bax protein levels, the corresponding commercial antibodies (Santa Cruz Biotechnology, Santa Cruz, Calif.) were used.

In the HT-29 human colon carcinoma cell line, the observed Bcl-2 level was low. Western blot analysis indicated that treatments with a composition comprising 50 $\mu$M PDC, 150 $\mu$M zinc, 100 $\mu$M EA, and 6 mM DMETN for 4 h. enhanced the expression of both p53 and Bax 2.0–2.5 fold, without changing the expression of Bcl-2. Similar results were obtained with MDA-MB-231 breast cancer cells. These experiments indicated that increased expression of apoptotic gene products plays an important role in the induction of rapid apoptotic cell death by the present compositions.

Example 24

In Vivo Acute Toxicological Investigations

Specified pathogen free (SPF) hygienic category first generation hybrid BDF1 (C57B1 female×DBA/2 male)

adult female mice weighing 22–23 g were used. The animals were kept in macrolon cages at 22–24 C (45–55% humidity), with a lighting regimen of 12/12 h light/dark. The animals had free access to tap water and were fed with a sterilized standard diet (Charles River VRF1, autoclavable) ad libitum.

Solutions of PDC (0.5–2 mM), zinc (0.5–2 mM), EA (0.5–2 mM), and DMETN (20–80 mM) were made up in physiological saline and injected intraperitoneally. The animals were followed for 21 days and evaluated based on survival and body weight. Seven animals were evaluated for each treatment.

At the above concentration ranges, PDC or EA alone were not toxic. 80 mM DMETN alone killed all seven animals after 3–4 days. However, 100% of the animals survived with no statistically significant loss in body weight after injecting compositions comprising 1 mM PDC, 1 mM zinc, 1 mM EA, and 40 mM DMETN. This composition concentration is 1 order of magnitude higher than that used for intratumoral applications. Thus, diffusion of the compositions from the tumor tissue to the adjacent or remote tissues will be unlikely to cause toxic effects. The toxicological data also suggest the compositions can be varied in concentration over a wide range without harmful consequences. Systemic administration will also be unlikely to result in toxic effects.

Although the present invention has been described with reference to preferred embodiments, workers skilled in the art will recognize that changes may be made in form and detail without departing from the spirit and scope of the invention. In addition, the invention is not to be taken as limited to all of the details thereof as modifications and variations thereof may be made without departing from the spirit or scope of the invention.

I claim:

1. A composition capable of inducing apoptosis or necrosis in cancer cells, comprising:
    a dithiocarbamate compound;
    a metal cation selected from the group consisting of $Zn^{++}$ and $Cu^{++}$;
    a modulator of cellular glutathione effective to decrease cellular glutathione levels, wherein the modulator of cellular glutathione is selected from the group consisting of ethacrynic acid, L-buthionine-S,R-sulfoximine, diethylmaleate, 2-cyclohexene-1-one, and 1-chloro-2,4-dinitrobenzene; and
    dimethylethanolamine.

2. The composition of claim 1, wherein the dithiocarbamate compound has the formula:

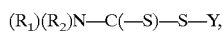

wherein $R_1$ and $R_2$ may be independently selected from the group consisting of hydrogen, C1–C24 straight, branched, or cyclic alkyl, alkenyl, aryl, acyl, alkaryl, aralkyl, and alkoxy groups, optionally substituted with ester, ether, halogen, sulfate, hydroxy, or phosphate groups, and wherein $R_1$ and $R_2$ may be optionally connected via a bridge comprising —$(CH_2)_n$—, wherein n is 3–8, and wherein said bridge may be optionally substituted independently on any of the carbon atoms with C1–C10 straight, branched, or cyclic alkyl, aryl, aralkyl, or alkaryl groups, each of said groups optionally substituted with hydroxy, halo, phosphate, sulfate, or sulfonate groups; and
    wherein Y is chosen from the group consisting of hydrogen, a pharmaceutically acceptable cation, a physiologically cleavable leaving group, a targeting moiety, and a chemotherapeutic drug.

3. The composition of claim 1, wherein the dithiocarbamate compound is selected from the group consisting of: diethyldithiocarbamate; tetraethylthiuram disulfide; and pyrrolidinedithiocarbamate.

4. The composition of claim 1, wherein the dithiocarbamate compound is pyrrolidinedithiocarbamate.

5. The composition of claim 1, wherein the metal cation is $Zn^{++}$.

6. The composition of claim 1, wherein the modulator of cellular glutathione is ethacrynic acid.

7. The composition of claim 1, wherein the dithiocarbamate compound is pyrrolidinedithiocarbamate in a concentration range of about 5–200 $\mu$M, wherein the metal cation is $Zn^{++}$ in a concentration range of about 20–500 $\mu$M, wherein the modulator of cellular glutathione is ethacrynic acid in a concentration range of about 10–300 $\mu$M, and wherein dimethylethanolamine is in a concentration range of about 3–40 mM.

8. A composition capable of inducing apoptosis or necrosis in cancer cells, comprising:
    a biologically effective amount of a dithiocarbamate compound; and
    a biologically effective amount of a modulator of cellular glutathione effective to decrease cellular glutathione levels, wherein the modulator of cellular glutathione is selected from the group consisting of ethacrynic acid, L-buthionine-SR-sulfoximine, diethylmaleate, 2-cyclohexene-1-one, and 1-chloro-2,4-dinitrobenzene.

9. The composition of claim 8, wherein the dithiocarbamate compound is pyrrolidinedithiocarbamate.

10. The composition of claim 8, wherein the modulator of cellular glutathione is ethacrynic acid.

11. The composition of claim 8, wherein the dithiocarbamate compound is pyrrolidinedithiocarbamate, and the modulator of cellular glutathione is ethacrynic acid.

12. The composition of claim 11, comprising about 10 to about 50 $\mu$M pyrrolidinedithiocarbamate, and about 10 to about 50 $\mu$M ethacrynic acid.

13. The composition of claim 11, comprising about 20 $\mu$M pyrrolidinedithiocarbamate, and about 10 $\mu$M ethacrynic acid.

14. The composition of claim 8, further comprising a biologically effective amount of dimethylethanolamine.

15. A composition capable of inducing apoptosis or necrosis in cancer cells, comprising:
    a biologically effective amount of a dithiocarbamate compound;
    a biologically effective amount of a modulator of cellular glutathione effective to decrease cellular glutathione levels, wherein the modulator of cellular glutathione is selected from the group consisting of ethacrynic acid L-buthionine-S,R-sulfoximine, diethylmaleate, 2-cyclohexene-1-one and 1-chloro-2,4-dinitrobenzene; and
    a biologically effective amount of a metal cation selected from the group consisting of $Zn^{++}$ and $Cu^{++}$.

16. The composition of claim 15, wherein the dithiocarbamate compound is pyrrolidinedithiocarbamate.

17. The composition of claim 15, wherein the modulator of cellular glutathione is ethacrynic acid.

18. The composition of claim 15, wherein the metal cation is $Zn^{++}$.

19. The composition of claim 15, comprising about 5 to about 50 $\mu$M pyrrolidinedithiocarbamate, about 50 to about 200 $\mu$M $Zn^{++}$, and about 10 to about 100 $\mu$M ethacrynic acid.

20. The composition of claim 15, comprising about 10 to about 50 μM pyrrolidinedithiocarbamate, about 30 to about 80 μM $Zn^{++}$, and about 30 to about 80 μM ethacrynic acid.

21. A composition capable of inducing apoptosis or necrosis in cancer cells, comprising:
- a biologically effective amount of a dithiocarbamate compound;
- a biologically effective amount of a metal cation selected from the group consisting of $Zn^{++}$ and $Cu^{++}$; and
- a biologically effective amount of dimethyethanolamine.

22. The composition of claim 21, wherein the dithiocarbamate compound is pyrrolidinedithiocarbamate.

23. The composition of claim 21, wherein the metal cation is $Zn^{++}$.

24. A composition capable of inducing apoptosis or necrosis in cancer cells, comprising:
- tricyclo-[5.2.1.$O^{2,6}$]-decyl-9 [8]-xanthogenate; and
- a modulator of cellular glutathione effective to decrease cellular glutathione levels, wherein the modulator of cellular glutathione is selected from the group consisting of ethacrynic acid, L-buthionine-S,R-sulfoximine, diethylmaleate, 2-cyclohexene-1-one, and 1-chloro-2,4-dinitrobenzene.

25. The composition of claim 24, wherein the modulator of cellular glutathione is ethacrynic acid.

26. The composition of claim 24, further comprising dimethylethanolamine.

27. The composition of claim 24, further comprising a metal cation selected from the group consisting of $Zn^{++}$ and $Cu^{++}$.

28. The composition of claim 27, wherein the metal cation is $Zn^{++}$.

29. The composition of claim 24, wherein the modulator of cellular glutathione is ethacrynic acid, and wherein the composition further comprises dimethylethanolamine and $Zn^{++}$.

* * * * *

UNITED STATES PATENT AND TRADEMARK OFFICE
CERTIFICATE OF CORRECTION

PATENT NO.    : 6,756,063 B2
DATED         : June 29, 2004
INVENTOR(S)   : Zoltan Kiss It is certified that error appears in the above-identified patent and that said Letters Patent is hereby corrected as shown below:

Column 25,
Line 50, that portion of the formula reading "C(–S)" should read -- C(=S) --.

Column 26,
Line 28, delete the word "L-buthionine-SR-sulfoximine," and replace it with -- L-buthionine-S,R-sulfoximine, --
Line 55, delete the word "2-cyclohexene-1-one" and replace it with -- 2-cyclohexene-1-one, --

Signed and Sealed this

Sixteenth Day of November, 2004

JON W. DUDAS
*Director of the United States Patent and Trademark Office*